(12) United States Patent
Dotson et al.

(10) Patent No.: US 8,653,098 B2
(45) Date of Patent: Feb. 18, 2014

(54) PYRAZOLOPYRIDINE PI3K INHIBITOR COMPOUNDS AND METHODS OF USE

(75) Inventors: Jennafer Dotson, Belmont, CA (US); Timothy Heffron, Burlingame, CA (US); Alan G. Olivero, Half Moon Bay, CA (US); Daniel P. Sutherlin, Burlingame, CA (US); Steven Staben, San Francisco, CA (US); Shumei Wang, Foster City, CA (US); Bing-Yan Zhu, Palo Alto, CA (US); Irina S. Chuckowree, Basel (CH); Adrian J. Folkes, Basel (CH); Nan Chi Wan, Basel (CH)

(73) Assignee: Genentech, Inc., South San Francisco, CA (US)

( * ) Notice: Subject to any disclaimer, the term of this patent is extended or adjusted under 35 U.S.C. 154(b) by 314 days.

(21) Appl. No.: 13/129,091

(22) PCT Filed: Nov. 19, 2009

(86) PCT No.: PCT/US2009/065085
§ 371 (c)(1),
(2), (4) Date: Oct. 26, 2011

(87) PCT Pub. No.: WO2010/059788
PCT Pub. Date: May 27, 2010

(65) Prior Publication Data
US 2012/0035208 A1    Feb. 9, 2012

Related U.S. Application Data

(60) Provisional application No. 61/116,427, filed on Nov. 20, 2008.

(51) Int. Cl.
*A61K 31/44* (2006.01)
*C07D 491/02* (2006.01)
*C07D 498/02* (2006.01)

(52) U.S. Cl.
USPC .......................................... 514/303; 546/119

(58) Field of Classification Search
USPC .......................................... 514/303; 546/119
See application file for complete search history.

(56) References Cited

U.S. PATENT DOCUMENTS

| | | | |
|---|---|---|---|
| 3,403,158 A | 9/1968 | Markillie | |
| 3,894,005 A | 7/1975 | Hoehn et al. | |
| 4,115,394 A * | 9/1978 | Hoehn et al. | 546/119 |
| 4,182,887 A | 1/1980 | Roch et al. | |
| 4,224,322 A | 9/1980 | Roch et al. | |
| 4,260,621 A | 4/1981 | Roch et al. | |
| 6,245,769 B1 | 6/2001 | Arvanitis et al. | |
| 6,291,505 B1 | 9/2001 | Huebner et al. | |
| 6,727,273 B2 | 4/2004 | Huebner et al. | |
| 6,962,915 B2 | 11/2005 | Das et al. | |
| 7,056,354 B2 | 6/2006 | Fessmann et al. | |
| 7,186,710 B2 | 3/2007 | Sterk et al. | |
| 7,217,710 B2 | 5/2007 | Adams et al. | |
| 7,223,766 B2 | 5/2007 | Dugar et al. | |
| 7,846,929 B2 | 12/2010 | Folkes et al. | |
| 2005/0130954 A1 | 6/2005 | Mitchell et al. | |
| 2006/0128729 A1 | 6/2006 | Pal et al. | |
| 2007/0155716 A1 | 7/2007 | Simmen et al. | |
| 2007/0293516 A1 | 12/2007 | Knight et al. | |
| 2008/0032960 A1 | 2/2008 | Shokat et al. | |
| 2008/0171761 A1 | 7/2008 | Iino et al. | |
| 2008/0188482 A1 | 8/2008 | Rice et al. | |
| 2009/0124621 A1 | 5/2009 | Pellecchia | |
| 2009/0270426 A1 | 10/2009 | Shokat et al. | |
| 2009/0306126 A1 | 12/2009 | Foote et al. | |
| 2010/0009963 A1 | 1/2010 | Knight et al. | |
| 2010/0160255 A1 | 6/2010 | Kamata et al. | |
| 2011/0172216 A1 | 7/2011 | Dotson et al. | |

FOREIGN PATENT DOCUMENTS

| | | |
|---|---|---|
| WO | 2007/144202 A1 | 12/2007 |
| WO | 2007/144204 A1 | 12/2007 |
| WO | 2008/088692 A2 | 7/2008 |
| WO | 2009/145357 A1 | 12/2009 |

OTHER PUBLICATIONS

Braendvang et al., "Efficient and regioselective N-1 alkylation of 4-chloropyrazolo[3,4-d]pyrimidine" Tetrahedron Letters 48:3057-59 ( 2007).
Briel et al., "Synthese substituierter 6-Phenylpyrazolo[3,4-d]pyrimidine mit potenziell Adenosin-A2A-antagonischer Wirkung" Pharmazie 60:732-5 ( 2005).
Burch, "Nitrofuryl Heterocycles. VII. 4-Amino-6-(5-nitro-2-furyl)-1H-pyrazolo[3,4-d]pyrimidines" J. Med. Chem. 11(1):79-83 ( 1967).
Chern et al., "Design, synthesis, and structure-activity relationships of pyrazolo[3,4-d]pyrimidines: a novel class of potent enterovirus inhibitors" Bioorganic & Med. Chem. Letters 14:2519-25 ( 2004).
Dhainaut et al., "New Purines and Purine Analogs as Modulators of Multidrug Resistance" J. Med. Chem. 39:4099-4108 ( 1996).
Diaz-Ortiz et al., "Synthesis of Pyrazolo[3,4-b]pyridines by Cycloaddition Reactions under Microwave Irradiation" Tetrahedron 56(11):1569-77 ( 2000).

(Continued)

*Primary Examiner* — Niloofar Rahmani
(74) *Attorney, Agent, or Firm* — Alex Andrus; Genentech, Inc.

(57) ABSTRACT

Compounds of Formula (I), and including stereoisomers, geometric isomers, tautomers, solvates, metabolites and pharmaceutically acceptable salts thereof, are useful for inhibiting lipid kinases including p110 alpha and other isoforms of PI3K, and for treating disorders such as cancer or inflammation mediated by lipid kinases. Methods of using compounds of Formula (I) for in vitro, in situ, and in vivo diagnosis, prevention or treatment of such disorders in mammalian cells, or associated pathological conditions, are disclosed.

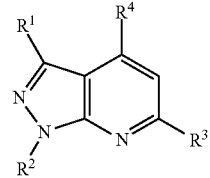

(I)

23 Claims, No Drawings

(56) References Cited

OTHER PUBLICATIONS

Diaz-Ortiz, "First Diels-Alder Reaction of Pyrazolyl Imines under Microwave Irradiation" Synlett 10:1069-70 ( 1998).

Dooley et al., "Theoretical Structure-Activity Studies of Adenosine A1 Ligands: Requirements for Receptor Affinity" Bioorganic & Med. Chem. 4(6):923-34 ( 1996).

Dooley, "Conformational Search for the N6-Substituted Adenosine Analogues and Related Adenosine A1 Receptor Antagonists" Bioorganic & Med. Chem. 4(6):917-21 ( 1996).

Goda et al., "Synthesis, antimicrobial activity and conformational analysis of novel substituted pyridines: BF3-promoted reaction of hydrazine with 2-alkoxy pyridines" Bioorganic & Medicinal Chemistry 12(8):1845-52 ( 2004).

Gonzalez et al., "Acylation D'Aminopyrazoles: Formation De Pyrazolo[3,4-b]Pyridines, Pyrazol0[3,4-d)Pyrimidines Et Dipyrazol0[3,4-b : 4',3'-e]Pyridines" Tetrahedron 34:1175-78 ( 1978).

Holla et al., "Synthesis of some novel pyrazolo[3,4-d]pyrimidine derivatives as potential antimicrobial agents" Bioorganic & Med. Chem. 14:2040-47 ( 2006).

Katiyar et al., "Facile Synthesis of Pyrazolo[3,4-d]pyrimidines and Pyrimido[4,5-d]pyrimidin-4-one Derivatives" Synthetic Comm. 36:2963-73 ( 2006).

Krishnaiah et al., "A novel approach to the synthesis of 5-trifluoromethyl-3-substituted pyrazoles" Journal of Fluorine Chemistry 115(1):9-11 ( 2002).

Peat et al., "Novel pyrazolopyrimidine derivatives as GSK-3 inhibitors" Bioorganic & Med. Chem. Letters 14:2121-24 ( 2004).

Southwick et al., "Preparation of 4,6-Diaminopyrazolo[3,4-d]pyrimidines with Variations in Substitution at the 1- and 3-Positions (1)" Jour. Heterocyclic Chem. 12(6):1199-1205 ( 1975).

Staben et al., "Structure-based optimization of pyrazolo-pyrimidine and -pyridine inhibitors of PI3-kinase" Bioorganic & Medicinal Chemistry Letters 20:6048-51 ( 2010).

Subramanyam et al., "6-(4-Pyridinyl)-1H-1,2,3-triazolo[4,5-d]pyrimidin-4(5H)-one: A Structurally Novel Competitive AMPA Receptor Antagonist" J. Med. Chem. 38:587-89 ( 1995).

Tan et al., "Traceless Solid-Phase Synthesis and Biological Evaluation of Purine Analogs as Inhibitors of Multidrug Resistance Protein 4" J. Comb. Chem. 9:210-18 ( 2007).

Tanaka et al., "Single Domain Intracellular Antibodies: A Minimal Fragment for Direct In Vivo Selection of Antigen-specific Intrabodies" Molecular Simulation 33(14-15):1109-17 ( 2007).

Van Haverbeke et al., "Synthesis of 1H-pyrazolo[3,4-b]pyridines and of pyrazolo[1,5-a]pyrimidines" Journal of Heterocyclic Chemistry 16(4):773-7 ( 1979).

Volochnyuk et al., "Electron-Rich Amino Heterocycles for Regiospecific Synthesis of Trifluoromethyl-Containing Fused Pyridines" Synthesis 10:1531-40 ( 2003).

\* cited by examiner

PYRAZOLOPYRIDINE PI3K INHIBITOR COMPOUNDS AND METHODS OF USE

This application claims priority to U.S. Provisional Ser. No. 61/116,427 filed on 20 Nov. 2008, the entire contents of which are incorporated by reference.

FIELD OF THE INVENTION

The invention relates generally to compounds with anti-cancer activity or anti-inflammation effects, and more specifically to compounds which inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Phosphatidylinositol (hereinafter abbreviated as "PI") is one of a number of phospholipids found in cell membranes. In recent years it has become clear that PI plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60).

Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

The main PI3-kinase isoform in cancer is the Class I PI3-kinase, p110 α (alpha) (U.S. Pat. No. 5,824,492; U.S. Pat. No. 5,846,824; U.S. Pat. No. 6,274,327). Other isoforms are implicated in cardiovascular and immune-inflammatory disease (Workman P (2004) Biochem Soc Trans 32:393-396; Patel et al (2004) Proceedings of the American Association of Cancer Research (Abstract LB-247) 95th Annual Meeting, March 27-31, Orlando, Fla., USA; Ahmadi K and Waterfield Md. (2004) Encyclopedia of Biological Chemistry (Lennarz W J, Lane M D eds) Elsevier/Academic Press).

The PI3 kinase/Akt/PTEN pathway is an attractive target for cancer drug development since such agents would be expected to inhibit proliferation, reverse the repression of apoptosis and surmount resistance to cytotoxic agents in cancer cells (Garcia-Echeverria et al (2008) Oncogene 27:5511-5526). PI3 kinase inhibitors have been reported (Folkes et al (2008) Jour. Med. Chem. 51:5522-5532; Belvin et al, American Association for Cancer Research Annual Meeting 2008, 99th: April 15, Abstract 4004; Folkes et al, American Association for Cancer Research Annual Meeting 2008, 99th: April 14, Abstract LB-146; Friedman et al, American Association for Cancer Research Annual Meeting 2008, 99th: April 14, Abstract LB-110; Yaguchi et al (2006) Jour. of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; U.S. Pat. No. 6,703,414; WO 97/15658; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070). including p110 alpha binding activity (US 2008/0207611; US 2008/0039459; US 2008/0076768; US 2008/0269210; US 2008/0242665).

SUMMARY OF THE INVENTION

The invention relates generally to pyrazolo[3,4-b]pyridine compounds of Formula I with anti-cancer activity, and more specifically with PI3 kinase inhibitory activity. Certain hyperproliferative disorders are characterized by the modulation of PI3 kinase function, for example by mutations or overexpression of the proteins. Accordingly, the compounds of the invention may be useful in the treatment of hyperproliferative disorders such as cancer or inflammation related disorders such as rheumatoid arthritis. The compounds may inhibit tumor growth in mammals and may be useful for treating human cancer patients.

The invention also relates to methods of using the pyrazolo[3,4-b]pyridines compounds of Formula I for in vitro, in situ, and in vivo diagnosis or treatment of mammalian cells, organisms, or associated pathological conditions.

Formula I compounds include:

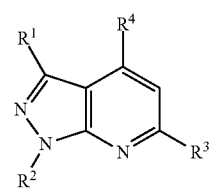

and stereoisomers, geometric isomers, tautomers, or pharmaceutically acceptable salts thereof. The various substituents $R^1$, $R^2$, $R^3$, $R^4$ are as defined herein.

Another aspect of the invention provides a pharmaceutical composition comprising a 1,3,4,6-substituted pyrazolo[3,4-b]pyridine compound of Formula I and a pharmaceutically acceptable carrier. The pharmaceutical composition may further comprise one or more additional therapeutic agent.

Another aspect of the invention provides methods of inhibiting PI3 kinase activity, comprising contacting a PI3 kinase with an effective inhibitory amount of a compound of Formula I.

Another aspect of the invention provides methods of preventing or treating a hyperproliferative disease or disorder modulated by PI3 kinases, comprising administering to a mammal in need of such treatment an effective amount of a compound of Formula I. Examples of such hyperproliferative disease or disorder include, but are not limited to, cancer.

Another aspect of the invention provides methods of preventing or treating a hyperproliferative disorder, comprising administering to a mammal in need of such treatment an effective amount of a compound of Formula I, alone or in combination with one or more additional compounds having anti-hyperproliferative properties.

Another aspect of the invention provides methods of preventing or treating a inflammation disorder, comprising administering to a mammal in need of such treatment an effective amount of a compound of Formula I, alone or in combination with one or more additional compounds having anti-hyperproliferative properties.

In a further aspect the present invention provides a method of using a compound of this invention to treat a hyperproliferative disease or condition modulated by PI3 kinase in a mammal.

An additional aspect of the invention is the use of a compound of this invention in the preparation of a medicament for the treatment or prevention of a disease or condition modulated by PI3 kinase in a mammal.

Another aspect of the invention includes kits comprising a compound of Formula I, a container, and optionally a package insert or label indicating a treatment.

Another aspect of the invention includes methods of preparing, methods of separating, and methods of purifying compounds of Formula I.

Another aspect of the invention includes novel intermediates useful for preparing Formula I compounds.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)_2$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted, and includes radicals having "cis" and "trans" orientations, or alternatively, "E" and "Z" orientations. Examples include, but are not limited to, ethylenylene or vinylene (—CH=CH—), allyl (—$CH_2$CH=CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted. Examples include, but are not limited to, ethynyl (—C≡CH), propynyl (propargyl, —$CH_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynyl radical may be optionally. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted, for example, with oxo (=O), mercapto, or amino, etc. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyclo[3.1.0]hexanyl, 3-azabicyclo[4.1.0]heptanyl, azabicyclo[2.2.2]hexanyl, 3H-indolyl quinolizinyl 1H-benzo[d]imidazol-2(3H)-one-5-yl, and N-pyridyl ureas. Spiro moieties are also included within the scope of this definition. Examples of a heterocyclic group substituted with one or more oxo (=O) moieties are pyrimidinonyl and 1,1-dioxothiomorpholinyl.

The term "heteroaryl" refers to a monovalent aromatic radical of 5-, 6-, or 7-membered rings, and includes fused ring systems (at least one of which is aromatic) of 5 to about 20 ring atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted.

The heterocycle or heteroaryl groups may be carbon (carbon-linked), or nitrogen (nitrogen-linked) bonded to the pyrazolo[3,4-b]pyridine where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "monocyclic heteroaryl" refers to a five- or six-membered, unsubstituted or substituted, monocyclic heteroaryl radical which contains 1, 2, 3 or 4 ring heteroatoms independently selected from N, O and S. Any carbon (carbon-linked) atom of the monocyclic heteroaryl may be attached to the C-4 position as $R^4$ or at the C-6 position as $R^3$ of the pyridine ring according to Formula I. Monocyclic heteroaryl radicals include, but are not limited to: 2-pyridyl, 3-pyridyl, 4-pyridyl, 3-isoxazolyl, 4-isoxazolyl, 5-isoxazolyl, 2-imidazolyl, 4-imidazolyl, 3-pyrazolyl, 4-pyrazolyl, 2-pyrrolyl, 3-pyrrolyl, 2-thiazolyl, 4-thiazolyl, 5-thiazolyl, 3-pyridazinyl, 4-pyridazinyl, 5-pyridazinyl, 2-pyrimidinyl, 5-pyrimidinyl, 6-pyrimidinyl, 2-pyrazinyl, 2-oxazolyl, 4-oxazolyl, 5-oxazolyl, 2-furanyl, 3-furanyl, 2-thienyl, 3-thienyl, 3-triazolyl, 1-triazolyl, 5-tetrazolyl, 1-tetrazolyl, and 2-tetrazolyl. Monocyclic heteroaryls are optionally substituted.

"Fused bicyclic $C_4$-$C_{20}$ heterocyclyl" and "Fused bicyclic $C_1$-$C_{20}$ heteroaryl" containing one or more heteroatoms independently selected from nitrogen, oxygen, and sulfur, differ only by their aromatic character, and have two rings fused together, i.e. share a common bond. Any carbon (carbon-linked) atom of the bicyclic heterocyclyl and heteroaryl radicals may be attached to the C-4 position as $R^4$ or at the C-6 position as $R^3$ of the pyridine ring according to Formula I. Fused bicyclic heterocyclyl and heteroaryl radicals include, but are not limited to: 1H-indazole, 1H-indole, indolin-2-one, 1-(indolin-1-yl)ethanone, 1H-benzo[d][1,2,3]triazole, 1H-pyrazolo[3,4-b]pyridine, 1H-pyrazolo[3,4-d]pyrimidine, 1H-benzo[d]imidazole, 1H-benzo[d]imidazol-2(3H)-one, 1H-pyrazolo[3,4-c]pyridine, 1H-pyrrolo[2,3-c]pyridine, 3H-imidazo[4,5-c]pyridine, 7H-pyrrolo[2,3-d]pyrimidine, 7H-purine, 1H-pyrazolo[4,3-d]pyrimidine, 5H-pyrrolo[3,2-d]pyrimidine, 2-amino-1H-purin-6(9H)-one, quinoline, quinazoline, quinoxaline, isoquinoline, isoquinolin-1(2H)-one, 3,4-dihydroisoquinolin-1(2H)-one, 3,4-dihydroquinolin-2(1H)-one, quinazolin-2(1H)-one, quinoxalin-2(1H)-one, 1,8-naphthyridine, pyrido[3,4-d]pyrimidine, pyrido[3,2-b]pyrazine, benzo[d][1,3]dioxole, and 2,3-dihydrobenzo[b][1,4]dioxine.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkyating agents, antimetabolites, spindle poison plant alkaloids, cytoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10$^{-9}$, Pfizer), cisplatin (cis-diamine,dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., "McGraw-Hill Dictionary of Chemical Terms" (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Pyrazolo[3,4-b]pyridine Compounds

The present invention provides pyrazolo[3,4-b]pyridine compounds, and pharmaceutical formulations thereof, which are potentially useful in the treatment of diseases, conditions and/or disorders modulated by PI3 kinases. More specifically, the present invention provides compounds of Formula I

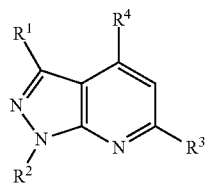

I and stereoisomers, geometric isomers, tautomers, or pharmaceutically acceptable salts thereof, wherein:

$R^1$ is selected from H, $C_1$-$C_{12}$ alkyl, —C(=O)$NR^{10}R^{11}$, —$NR^{12}$C(=O)$R^{10}$—, $NR^{12}$C(=O)$OR^{11}$, —$NR^{12}$C(=O)$NR^{10}R^{11}$, and $C_1$-$C_{20}$ heteroaryl where $C_1$-$C_{20}$ heteroaryl is optionally substituted with one or more groups independently selected from $C_1$-$C_{12}$ alkyl, $C_1$-$C_{12}$ alkyl-$NR^{10}R^{11}$, $C_1$-$C_{12}$ alkyl-$OR^{10}$, $C_6$-$C_{20}$ aryl, F, Cl, Br, I, —CN, —$CF_3$, —$CO_2H$, —C(=O)$NR^{10}R^{11}$, —$NO_2$, $NR^{10}R^{11}$, $NHCOR^{10}$, —$OR^{10}$, —S(O)$_2NR^{10}R^{11}$ and —S(O)$_2R^{10}$;

$R^2$ is $C_1$-$C_{12}$ alkyl;

$R^3$ is selected from carbon-linked $C_2$-$C_{20}$ heterocyclyl and carbon-linked $C_1$-$C_{20}$ heteroaryl, where carbon-linked $C_2$-$C_{20}$ heterocyclyl and carbon-linked $C_1$-$C_{20}$ heteroaryl are optionally substituted with one or more groups independently selected from $C_1$-$C_{12}$ alkyl, $C_6$-$C_{20}$ aryl, F, Cl, Br, I, —$CH_3$, —CN, —$CF_3$, —$CH_2OH$, —$CO_2H$, —$CONH_2$, —CON($CH_3$)$_2$, —$NO_2$, —$NH_2$, —$NHCH_3$, —$NHCOCH_3$, —OH, —$OCH_3$, —SH, —NHC(=O)$NHCH_3$, and —S(O)$_2CH_3$;

$R^4$ is selected from —$NR^{10}R^{13}$, —$NR^{12}$C(=O)$R^{10}$, —$NR^{10}$($C_1$-$C_{12}$ alkyl)$NR^{10}R^{13}$, —$NR^{10}$($C_1$-$C_{12}$ alkyl)$OR^{10}$, —$NR^{10}$($C_1$-$C_{12}$ alkyl)C(=O)$NR^{10}R^{13}$, —$NR^{10}$($C_1$-$C_{12}$ alkylene)-($C_3$-$C_{12}$ carbocyclyl), —$NR^{10}$($C_1$-$C_{12}$ alkylene)-($C_2$-$C_{20}$ heterocyclyl), —$NR^{10}$($C_1$-$C_{12}$ alkylene)-($C_6$-$C_{20}$ aryl), —$NR^{10}$($C_1$-$C_{12}$ alkylene)-($C_1$-$C_{20}$ heteroaryl), —$OR^{10}$, —O($C_1$-$C_{12}$ alkylene)-($C_3$-$C_{12}$ carbocyclyl), —O($C_1$-$C_{12}$ alkylene)-($C_2$-$C_{20}$ heterocyclyl), —O($C_1$-$C_{12}$ alkylene)-($C_6$-$C_{20}$ aryl), —O($C_1$-$C_{12}$ alkylene)-($C_1$-$C_{20}$ heteroaryl), —($C_1$-$C_{12}$ alkylene)$NR^{10}R^{13}$, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-($C_6$-$C_{20}$ aryl), —($C_1$-$C_{12}$ alkylene)-($C_1$-$C_{20}$ heteroaryl), —($C_2$-$C_8$ alkynylene)$NR^{10}R^{13}$, —($C_2$-$C_8$ alkynylene)-($C_3$-$C_{12}$ carbocyclyl), —($C_2$-$C_8$ alkynylene)-($C_2$-$C_{20}$ heterocyclyl), —($C_2$-$C_8$ alkynylene)-($C_6$-$C_{20}$ aryl), —($C_2$-$C_8$ alkynylene)-($C_1$-$C_{20}$ heteroaryl), —($C_1$-$C_{12}$ alkylene)-($C_6$-$C_{20}$ arylene)-($C_2$-$C_{20}$ heterocyclyl), —($C_6$-$C_{20}$ aryl)-($C_1$-$C_{12}$ alkylene)-($C_2$-$C_{20}$ heterocyclyl), —C(=O)$NR^{10}R^{11}$, $C_1$-$C_{12}$ alkyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl, where alkyl, alkylene, alkynyl, alkynylene, carbocyclyl, heterocyclyl, aryl, and heteroaryl are optionally substituted with one or more groups independently selected from F, Cl, Br, I, —$CH_3$, —$CH_2OH$, —CN, —$CF_3$, —$CO_2H$, —$COCH_3$, —$CONH_2$, —$CONHCH_3$, —CON($CH_3$)$_2$, —$NO_2$, —$NH_2$, —$NHCH_3$, —$NHCOCH_3$, —$NHS(O)_2CH_3$, —OH, —$OCH_3$, —S(O)$_2N(CH_3)_2$, —$SCH_3$, —$CH_2OCH_3$, and —S(O)$_2CH_3$;

$R^{10}$, $R^{11}$ and $R^{12}$ are independently selected from H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl, where alkyl, alkenyl, alkynyl, carbocyclyl, heterocyclyl, aryl, and heteroaryl are optionally substituted with one or more groups independently selected from F, Cl, Br, I, —$CH_2OH$, —$CH_2C_6H_5$, —CN, —$CF_3$, —$CO_2H$, —$CONH_2$, —$CONHCH_3$, —$NO_2$, —N($CH_3$)$_2$, —$NHCOCH_3$, —$NHS(O)_2CH_3$, —OH, —$OCH_3$, —$OCH_2CH_3$, —S(O)$_2NH_2$, —$SCH_3$, —S(O)$CH_3$, —$CH_2OCH_3$, —$CH_3$, and —S(O)$_2CH_3$;

or $R^{10}$ and $R^{11}$ together with the nitrogen atom to which they are attached form a $C_2$-$C_{20}$ heterocyclyl ring; and $R^{13}$ is selected from $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl, where alkyl, alkenyl, alkynyl, carbocyclyl, heterocyclyl, aryl, and heteroaryl are optionally substituted with one or more groups independently selected from F, Cl, Br, I, —$CH_2OH$, —$CH_2C_6H_5$, —CN, —$CF_3$, —$CO_2H$, —$CONH_2$, —$CONHCH_3$, —$NO_2$, —N($CH_3$)$_2$, —$NHCOCH_3$, —$NHS(O)_2CH_3$, —OH, —$OCH_3$, —$OCH_2CH_3$, —S(O)$_2NH_2$, —$SCH_3$, —S(O)$CH_3$, —$OCH_2CH_2$—N($CH_3$)$_2$, and —S(O)$_2CH_3$;

or $R^{10}$ and $R^{13}$ together with the nitrogen atom to which they are attached form a $C_2$-$C_{20}$ heterocyclyl ring.

Exemplary embodiments include wherein $R^1$ is H or $CH_3$.

Exemplary embodiments include wherein $R^2$ is $CH_3$.

Exemplary embodiments include wherein $R^3$ is a monocyclic heteroaryl selected from pyridyl, isoxazolyl, imidazolyl, pyrazolyl, pyrrolyl, thiazolyl, pyridazinyl, pyrimidinyl, pyrazinyl, oxazolyl, oxadiazolyl, furanyl, thienyl, triazolyl, and tetrazolyl.

Exemplary embodiments include wherein $R^3$ is a fused bicyclic $C_4$-$C_{20}$ heterocyclyl or $C_1$-$C_{20}$ heteroaryl selected from

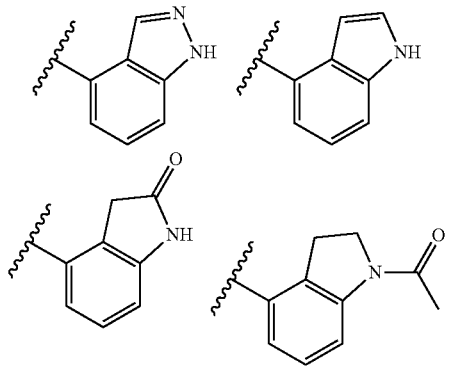

-continued
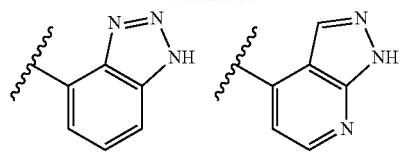
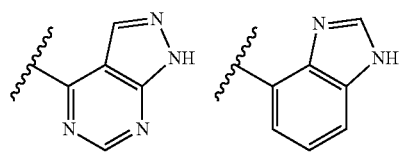
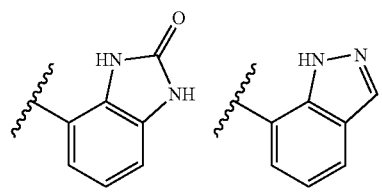
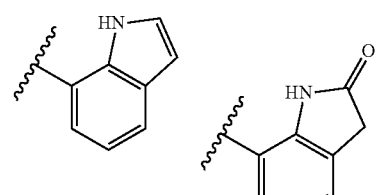
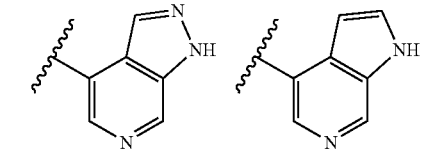
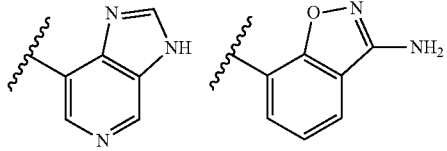
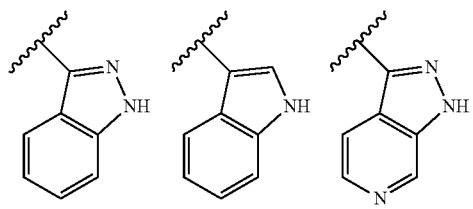
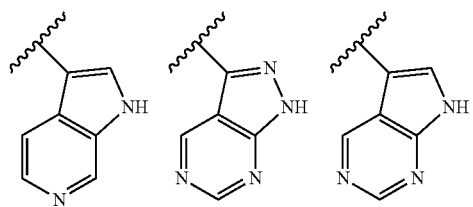
-continued
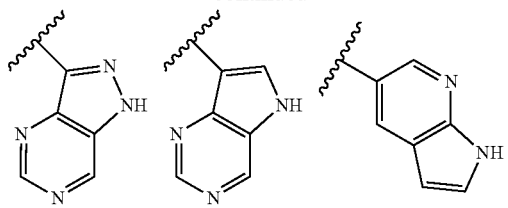
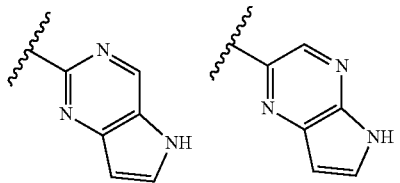
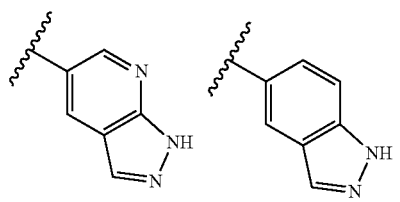
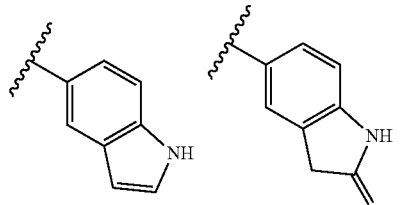
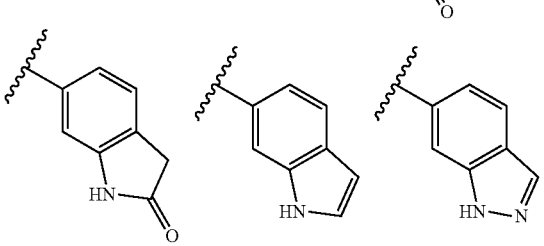
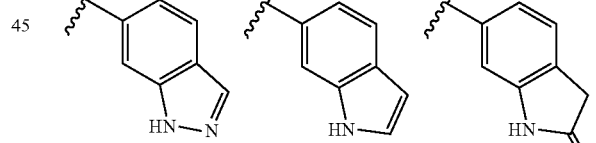
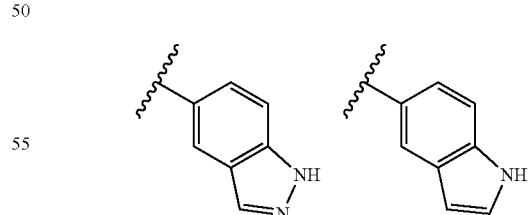
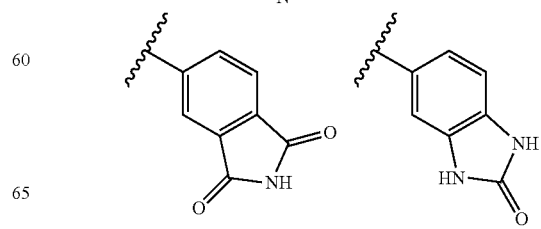

-continued

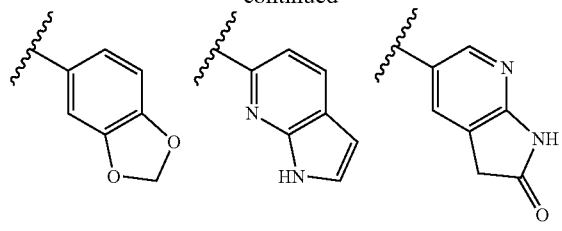

where the wavy line indicates the site of attachment.
Exemplary embodiments include wherein $R^3$ is selected from:

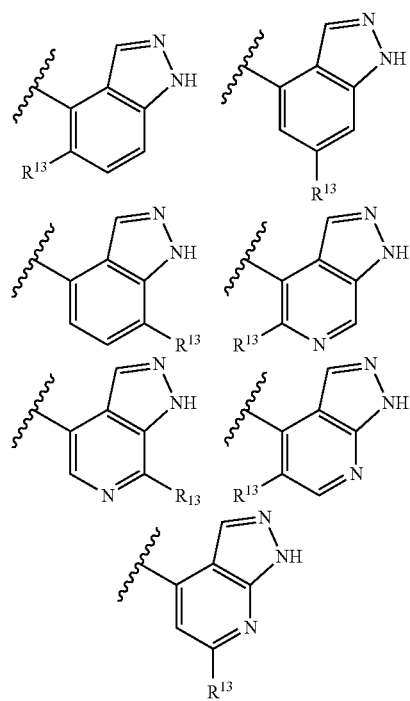

where the wavy line indicates the site of attachment.
Exemplary embodiments include wherein $R^3$ is a fused bicyclic $C_4$-$C_{20}$ heterocyclyl or $C_1$-$C_{20}$ heteroaryl selected from:

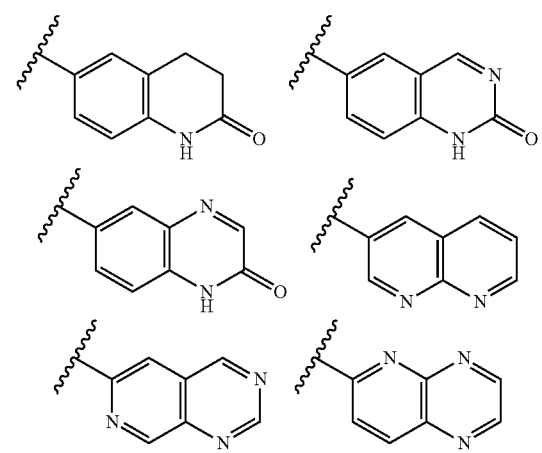

-continued

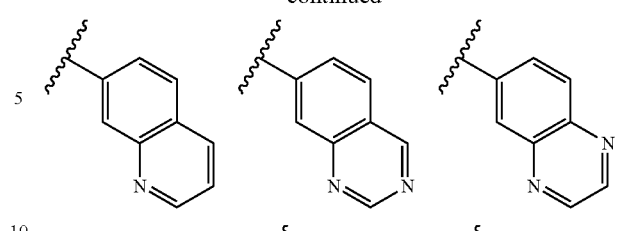

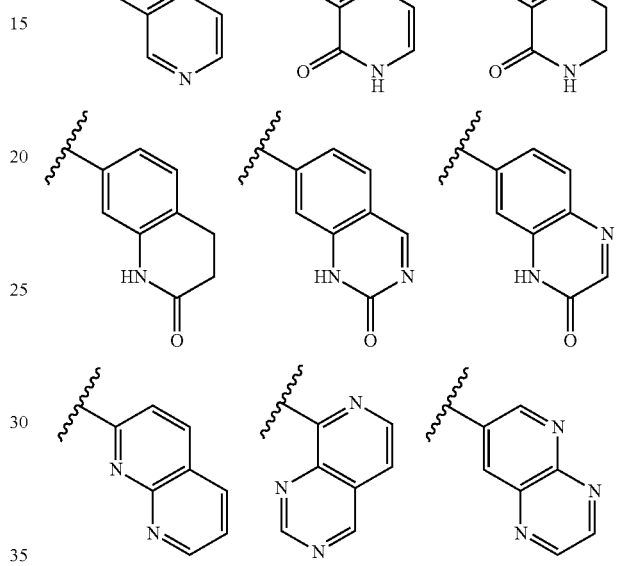

where the wavy line indicates the site of attachment.
Exemplary embodiments include wherein $R^3$ is 1H-indazol-4-yl or 1H-indol-4-yl.
Exemplary embodiments include wherein $R^3$ is a monocyclic heteroaryl selected from the structures:

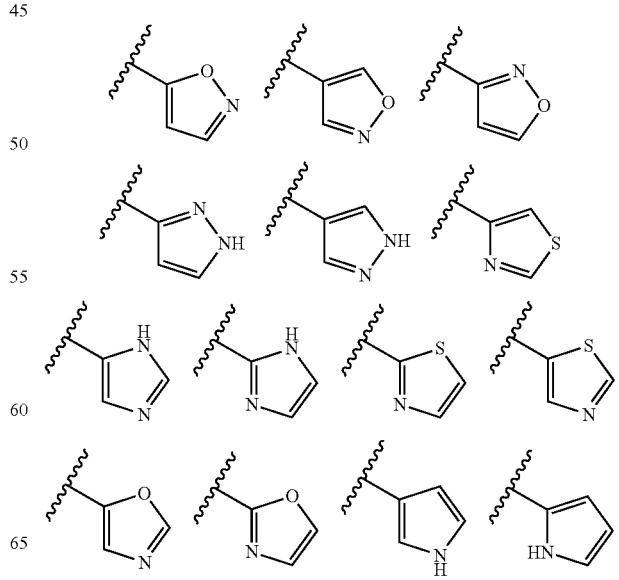

-continued

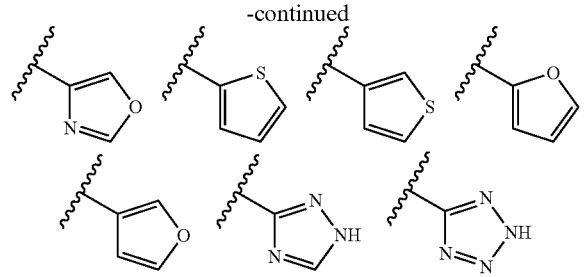

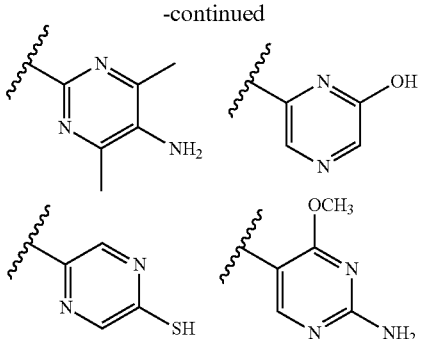

where the wavy line indicates the site of attachment.

Exemplary embodiments include wherein $R^3$ is a monocyclic heteroaryl selected from the structures:

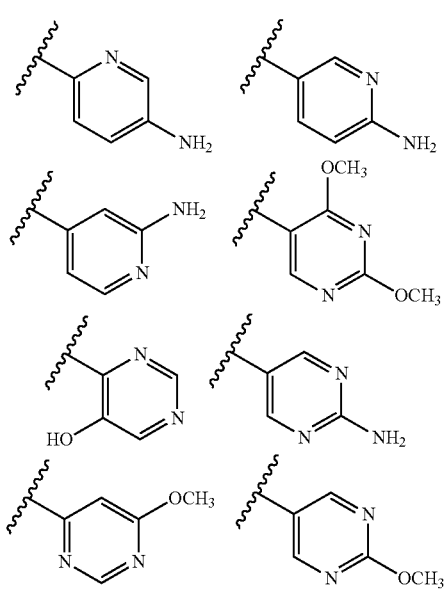

where the wavy line indicates the site of attachment.

Exemplary embodiments include wherein $R^3$ is a monocyclic heteroaryl selected from the structures:

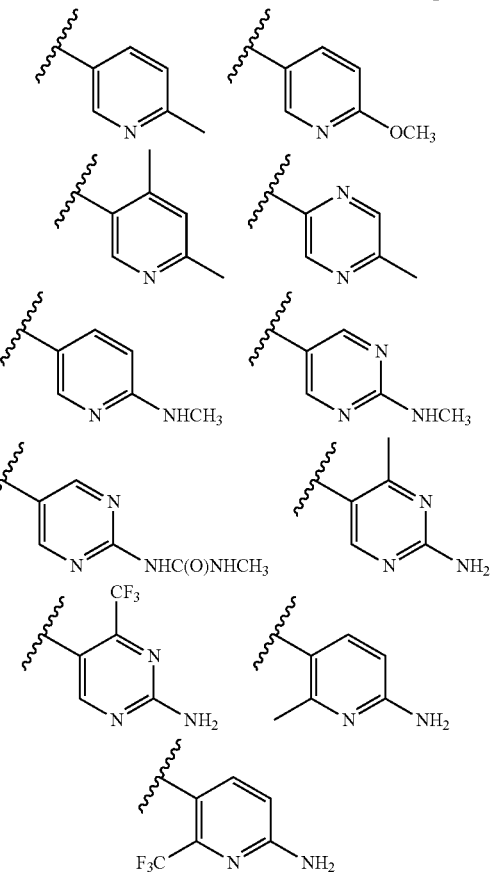

where the wavy line indicates the site of attachment.

Exemplary embodiments include wherein $R^3$ is a $C_1$-$C_{20}$ heteroaryl substituted with one or more groups selected from F, —$CF_3$, —$NH_2$, —$NHCH_3$, —OH, —$OCH_3$, —C(O)$CH_3$, —NHC(O)$CH_3$, —N(C(O)$CH_3$)$_2$, —NHC(O)$NH_2$, —$CO_2$H, —CHO, —$CH_2$OH, —C(═O)$NHCH_3$, —C(═O)$NH_2$, and —$CH_3$.

Exemplary embodiments include wherein $R^4$ is optionally substituted pyrimidin-5-yl, optionally substituted $C_6$-$C_{20}$ aryl, or optionally substituted phenyl.

Exemplary embodiments include wherein $R^4$ is —$OR^{10}$ where $R^{10}$ is optionally substituted phenyl.

Exemplary embodiments include wherein phenyl is substituted with one or more groups independently selected from —$OCH_3$, —$SO_2CH_3$, —$SO_2NH_2$, —$NHSO_2CH_3$, —$CH_2OCH_3$, —CN, —C(═O)$NH_2$, —C(═O)$NHCH_3$, —NHC(═O)$CH_3$, —$CF_3$, —OH, —$CH_3$, and —Cl.

Exemplary embodiments include wherein $R^4$ is —$OR^{10}$ where $R^{10}$ is optionally substituted pyridyl or optionally substituted $C_1$-$C_{12}$ alkyl.

Exemplary embodiments include wherein $R^4$ is —O($C_1$-$C_{12}$ alkylene)-($C_2$-$C_{20}$ heterocyclyl), —O($C_1$-$C_{12}$ alkylene)-($C_6$-$C_{20}$ aryl), or —O($C_1$-$C_{12}$ alkylene)-($C_1$-$C_{20}$ heteroaryl).

Exemplary embodiments include wherein $R^4$ is —$NR^{10}R^{13}$ where $R^{10}$ is H, $C_1$-$C_{12}$ alkyl, $C_2$-$C_8$ alkenyl, or $C_2$-$C_8$ alkynyl; and $R^{13}$ is optionally substituted phenyl, indazol-6-yl or indazol-4-yl.

Exemplary embodiments include wherein $R^4$ is —$NR^{10}$($C_1$-$C_{12}$ alkyl)$NR^{10}R^{13}$, —$NR^{10}$($C_1$-$C_{12}$ alkyl)$OR^{10}$, or —$NR^{10}$($C_1$-$C_{12}$ alkyl)C(=O)$NR^{10}R^{13}$.

Exemplary embodiments include wherein $R^4$ is —$NR^{10}R^{13}$ where $R^{10}$ and $R^{13}$ together with the nitrogen atom to which they are attached form morpholinyl, 4-methylpiperazin-1-yl, 4-methylsulfonylpiperazin-1-yl, or 4-(2-pyridyl)piperazin-1-yl.

The Formula I compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all geometric and positional isomers. For example, if a Formula I compound incorporates a double bond or a fused ring, the cis- and trans-forms, as well as mixtures thereof, are embraced within the scope of the invention. Both the single positional isomers and mixture of positional isomers are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^3H$ and $^{14}C$) are useful in compound and/or substrate tissue distribution assays. Tritiated ($^3H$) and carbon-14 ($^{14}C$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Preparation of Formula I Compounds

Pyrazolo[3,4-b]pyridines compounds of Formula I may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

In certain embodiments, compounds of Formula I may be readily prepared using well-known procedures to prepare pyrazolo[3,4-b]pyridines (Southwick et al (1975) J. of Heterocyclic Chem. 12(6):1199-1205; Van Haverbeke et al (1979) Jour. of Heterocyclic Chem. 16(4):773-777; Diaz-Ortiz et al (1998) Synlett 1069-1070; Diaz-Ortiz et al (2000) 56(11):1569-1577; Quintela et al (2001) European Journal of Medicinal Chemistry 36 (4), pp 321-332; Wu et al (2003) Organic Letters 5(20):3587-3590; Quintela et al (2003) Bioorganic & Med. Chem. 11(6):863-868; Kim et al (2003) European Journal of Medicinal Chemistry 38 (5), pp 525-532; Volochnyuk et al (2003) Synthesis 10:1531-1540; Goda et al (2004) Bioorganic & Med. Chem. 12(8):1845-1852; Chem et al (2004) Bioorganic & Med. Chem. Letters 14(10): 2519-2525; Katiyar et al (2006) Synthetic Communications 36(20):2963-2973; Holla et al (2006) Bioorganic & Medicinal Chemistry 14(6):2040-2047; Braendvang et al (2007) Tetrahedron Letters 48(17):3057-3059; U.S. Pat. No. 3,403, 158; U.S. Pat. No. 3,894,005; U.S. Pat. No. 4,001,230; U.S. Pat. No. 4,044,130; U.S. Pat. No. 4,115,394; U.S. Pat. No. 4,182,887; U.S. Pat. No. 6,291,505; U.S. Pat. No. 6,660,744; U.S. Pat. No. 6,921,763; U.S. Pat. No. 7,056,354; U.S. Pat. No. 7,217,710; US 2006/0128729; US 2007/0155716; WO 2005/117909; WO 2007/144204; WO 2007/144202); and other heterocycles, which are described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990).

Pyrazolo[3,4-b]pyridines have been prepared generally by cyclization reactions starting from different heterocyclic reagents (Hardy, C. R. (1984) Adv. Heterocycl. Chem. 36:343; Molina et al (1989) Chem. Ber. 122:307; Benoit et al (1987) Synthesis 1124; Bare et al (1989) J. Med. Chem. 32:2561; Sanghvi et al (1990) J. Chem. Soc., Perkin Trans. 1, 2943).

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

For illustrative purposes, General Procedures A-D show general methods for preparing Formula I compounds, as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, *Protective Groups in Organic Synthesis*, John Wiley & Sons, New York, 1991.

General Preparative Procedures
General Procedure A Suzuki Coupling at C-6

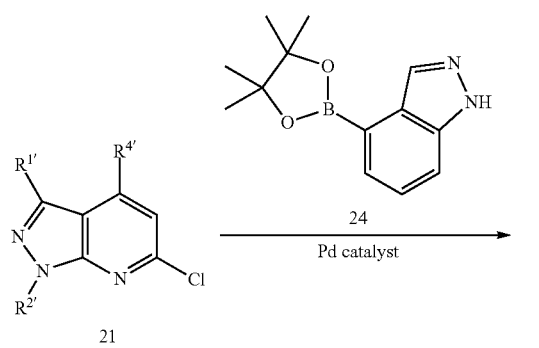

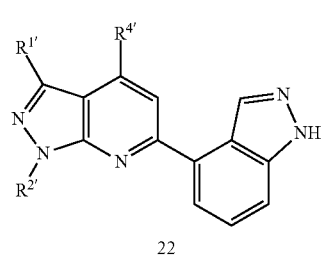

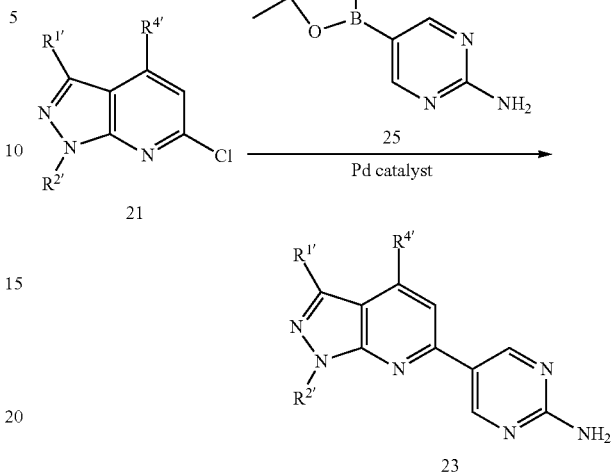

The Suzuki-type coupling reaction is useful to attach a monocyclic heteroaryl, a fused bicyclic heterocycle, or a fused bicyclic heteroaryl, at the 6-position of the pyridine ring of a 6-chloro-1H-pyrazolo[3,4-b]pyridine 21 compound. For example, 21 may be combined with about 1.5 equivalents of 4-(4,4,5,5-tetramethyl-1,3,2-dioxaborolan-2-yl)1H-indazole 24 (US 2008/0039459, US 2008/0076758) or 5-(4,4,5,5-tetramethyl-1,3,2-dioxaborolan-2-yl)pyrimidin-2-amine 25 (US 2008/0269210, US 2008/0242665), and dissolved in about 3 equivalents of sodium carbonate as a 1 molar solution in water and an equal volume of acetonitrile. A catalytic amount, or more, of a low valent palladium reagent, such as bis(triphenylphosphine)palladium(II) dichloride, is added. A variety of boronic acids or boronic esters can be used in place of the indazole boronic ester indicated. Also alternatively, the nitrogen of the indazole may be protected, for example N-THP. In some cases potassium acetate is used in place of sodium carbonate to adjust the pH of the aqueous layer. The reaction is then heated to about 140-150° C. under pressure in a microwave reactor such as the Biotage Optimizer (Biotage, Inc.) for 10 to 30 minutes. The contents are extracted with ethyl acetate, or another organic solvent. After evaporation of the organic layer the Suzuki coupling products, 1,3,4-substituted 6-(1H-indazol-4-yl)-1H-pyrazolo[3,4-b]pyridine 22, or 1,3,4-substituted 5-(1H-pyrazolo[3,4-b]pyridin-6-yl)pyrimidin-2-amine 23, may be purified on silica or by reverse phase HPLC. Substituents $R^{1'}$, $R^{2'}$, $R^{4'}$ may be $R^1$, $R^2$, $R^4$ as defined, or protected forms or precursors thereof.

Boronic ester (or acid) (1.5 eq) 24 or 25, and a palladium catalyst such as bis(triphenylphosphine)palladium(II) chloride (0.05 eq) is added to a mixture of chloro intermediate (1 eq) 21 in acetonitrile and 1 M of sodium carbonate aqueous solution (equal volume as acetonitrile). The reaction mixture is heated to 150° C. in a microwave for 15 min. LC/MS indicates when the reaction is complete. Water is added to the mixture, and the precipitated product is filtered and purified by HPLC to yield the product 22 or 23. Substituents $R^{1'}$, $R^{2'}$, $R^{4'}$ may be $R^1$, $R^2$, $R^4$ as defined, or protected forms or precursors thereof.

A variety of palladium catalysts can be used during the Suzuki coupling step to form compounds, including exemplary embodiments 22 and 23. Suzuki coupling is a palladium mediated cross coupling reaction of an arylhalide, such as 21, with a boronic acid such as 24 or 25. Various low valent, Pd(II) and Pd(0) catalysts may be used in the Suzuki coupling reaction, including PdCl2(PPh$_3$)$_2$, Pd(t-Bu)$_3$, PdCl$_2$ dppf CH$_2$Cl$_2$, Pd(PPh$_3$)$_4$, Pd(OAc)/PPh$_3$, Cl$_2$Pd[(Pet$_3$)]$_2$, Pd(DIPHOS)$_2$, Cl$_2$Pd(Bipy), [PdCl(Ph$_2$PCH$_2$PPh$_2$)]$_2$, Cl$_2$Pd [P(o-tol)$_3$]$_2$, Pd$_2$(dba)$_3$/P(o-tol)$_3$, Pd$_2$(dba)/P(furyl)$_3$, Cl$_2$Pd [P(furyl)$_3$]$_2$, Cl$_2$Pd(PMePh$_2$)$_2$, Cl$_2$Pd[P(4-F-Ph)$_3$]$_2$, Cl$_2$Pd[P (C$_6$F$_6$)$_3$]$_2$, Cl$_2$Pd[P(2-COOH-Ph)(Ph)$_2$]$_2$, Cl$_2$Pd[P(4-COOH-Ph)(Ph)$_2$]$_2$, and encapsulated catalysts Pd EnCat™ 30, Pd EnCat™ TPP30, and Pd(II) EnCat™ BINAP30 (US 2004/0254066).

General Procedure B 4-Chloro Substitution with Amine Reagents

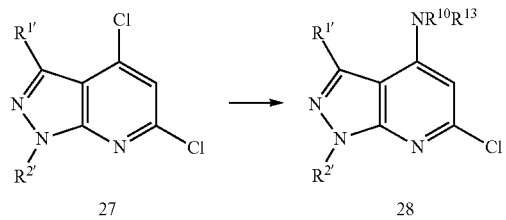

To a 4,6-dichloro pyrazolo[3,4-b]pyridine intermediate 27 in a solvent such as ethanol is added a primary or secondary amine (R$^{10}$R$^{13}$NH, 1.1 equiv.) and optionally a non-nucleophilic base such as triethylamine (NEt$_3$, 1.5 eq, 63 μl). Alternatively, acetonitrile may be used as the solvent and potassium carbonate may be used as the base. The reaction mixture is stirred at room temperature for about 1 hour or overnight, volatiles removed in vacuo and residue partitioned between DCM and brine. If the mixture is insoluble it may be sonicated and the solid product was collected by filtration. Drying with magnesium sulfate and evaporation of the solvent gives N'-(6-chloro pyrazolo[3,4-d]pyrimidin-4-yl)-amine substituted intermediate 28, often as a crystalline solid, or by trituration. Substituents R$^{1'}$ and R$^{2'}$ may be R$^1$ and R$^2$ as defined, or protected forms or precursors thereof.

General Procedure C Cyclization of 4-alkylcarboxylate, 5-amino-pyrazoles

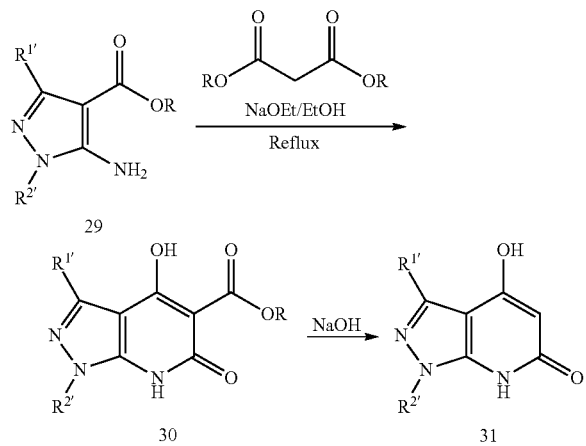

A general synthetic route to 1,3,4,6-substituted pyrazolo [3,4-b]pyridine compounds of Formula I begins with cyclization of an alkyl 5-amino-1-methylpyrazole-4-carboxylate 29 with a dialkylmalonate, such as diethylmalonate, under basic conditions such as sodium hydroxide in ethanol to give the to give the alkyl 4-hydroxy-6-oxo-6,7-dihydro-1H-pyrazolo[3, 4-b]pyridine-5-carboxylate compound 30 (R═C$_1$-C$_{12}$ alkyl). Saponification and decarboxylation give the 4-hydroxy-1H-pyrazolo[3,4-b]pyridine-6(7H)-one compound 31. Substituents R$^{1'}$ and R$^{2'}$ may be R$^1$ and R$^2$ as defined, or protected forms or precursors thereof.

General Procedure D Chlorination and Suzuki Coupling

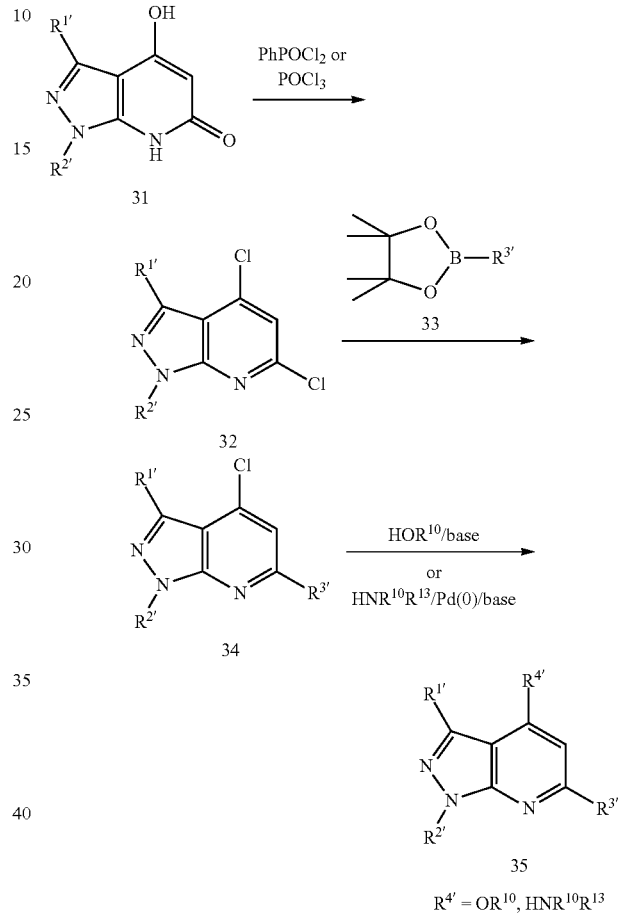

R$^{4'}$ = OR$^{10}$, HNR$^{10}$R$^{13}$

A general synthetic route to 6-heterocycle pyrazolo[3,4-b] pyridines 35 includes chlorination of a 4-hydroxy-1H-pyrazolo[3,4-b]pyridine-6(7H)-one compound 31 at the 2- and 4-positions with a chlorinating reagent such as a phosphorylchloride like phenylphosphoryldichloride or phosphoryltrichloride to give the 4,6-dichloro-1H-pyrazolo[3,4-b]pyridine intermediate 32. A Suzuki-type coupling reaction according to General Procedure A can attach a monocyclic heteroaryl, a fused bicyclic heterocycle, or a fused bicyclic heteroaryl, at the 6-position of the pyridine ring of 32 with a (4,4,5,5-tetramethyl-1,3,2-dioxaborolan-2-yl)heterocycle reagent, such as 24 or 25, and a palladium catalyst, such as bis(triphenylphosphine)palladium(II) chloride (0.05 eq) in acetonitrile and sodium carbonate aqueous solution. The reaction mixture is heated to about 150° C. in a microwave for about 15 min or more. LC/MS indicates when the reaction is complete. Water is added to the mixture, and the precipitated product is filtered and purified by HPLC to yield the 4-chloro-6-heterocycle-1H-pyrazolo[3,4-b]pyridine intermediate 34. The 4-chloro may be substituted with either alcohol (HOR$^{10}$) or amine (HNR$^{10}$R$^{13}$), primary or secondary, nucleophile reagents to give 6-heterocycle pyrazolo[3,4-b]pyridines 35 of Formula I. Substituents $R^{1'}, R^{2'}, R^{3'}, R^{4'}$ may be $R^1, R^2, R^{3'}, R^4$ as defined, or protected forms or precursors thereof.

Methods of Separation

In the methods of preparing the compounds of this invention, it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-13-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 1996/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Biological Evaluation

Determination of the activity of PI3 kinase activity of a compound of Formula I is possible by a number of direct and indirect detection methods. Certain exemplary compounds described herein were assayed for their PI3K binding activity (Example 32) and in vitro activity against tumor cells (Example 33). The range of PI3K binding activities was less than 1 nM (nanomolar) to about 10 μM (micromolar). Certain exemplary compounds of the invention had PI3K binding activity $IC_{50}$ values less than 10 nM. Certain compounds of the invention had tumor cell-based activity $IC_{50}$ values less than 100 nM.

The cytotoxic or cytostatic activity of Formula I exemplary compounds was measured by: establishing a proliferating mammalian tumor cell line in a cell culture medium, adding a Formula I compound, culturing the cells for a period from about 6 hours to about 5 days; and measuring cell viability (Example 33). Cell-based in vitro assays were used to measure viability, i.e. proliferation ($IC_{50}$), cytotoxicity ($EC_{50}$), and induction of apoptosis (caspase activation).

The in vitro potency of Formula I exemplary compounds was measured by the cell proliferation assay, CellTiter-Glo® Luminescent Cell Viability Assay, commercially available from Promega Corp., Madison, Wis. (Example 33). This homogeneous assay method is based on the recombinant expression of *Coleoptera* luciferase (U.S. Pat. No. 5,583,024;

U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 or 384 well had an $IC_{50}$ of 0.053 micromole; compound 108 had an $IC_{50}$ of 0.016 micromole; compound 117 had an $IC_{50}$ of 0.0475 micromole; compound 120 had an $IC_{50}$ of 0.575 micromole; and compound 121 had an $IC_{50}$ of 0.153 micromole

TABLE 1

| No. | Structure | Name |
|---|---|---|
| 101 | 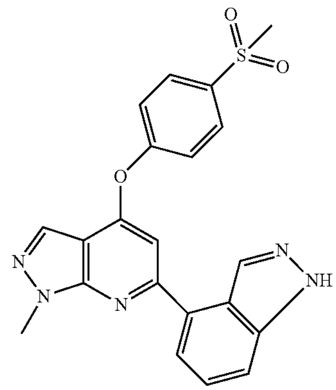 [SMILES: Cn1ncc2c(Oc3ccc(S(C)(=O)=O)cc3)cc(-c3cccc4[nH]ncc34)nc21] | 6-(1H-indazol-4-yl)-1-methyl-4-(4-(methylsulfonyl)phenoxy)-1H-pyrazolo[3,4-b]pyridine |
| 102 | 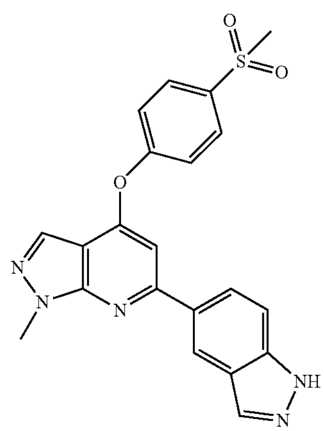 [SMILES: Cn1ncc2c(Oc3ccc(S(C)(=O)=O)cc3)cc(-c3ccc4[nH]ncc4c3)nc21] | 6-(1H-indazol-5-yl)-1-methyl-4-(4-(methylsulfonyl)phenoxy)-1H-pyrazolo[3,4-b]pyridine |
| 103 | 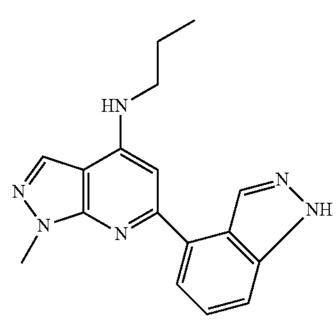 [SMILES: CCCNc1cc(-c2cccc3[nH]ncc23)nc2c1cnn2C] | 6-(1H-indazol-4-yl)-1-methyl-N-propyl-1H-pyrazolo[3,4-b]pyridin-4-amine |

TABLE 1-continued

| No. | Structure | Name |
|---|---|---|
| 104 | 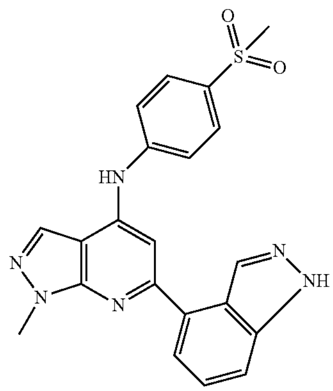 [SMILES: Cn1ncc2c(Nc3ccc(S(C)(=O)=O)cc3)cc(-c3cccc4[nH]ncc34)nc21] | 6-(1H-indazol-4-yl)-1-methyl-N-(4-(methylsulfonyl)phenyl)-1H-pyrazolo[3,4-b]pyridin-4-amine |
| 105 | 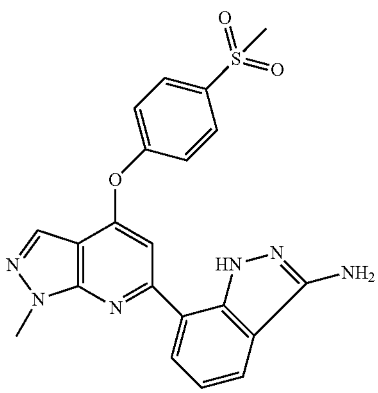 [SMILES: Cn1ncc2c(Oc3ccc(S(C)(=O)=O)cc3)cc(-c3cccc4c(N)n[nH]c34)nc21] | 7-(1-methyl-4-(4-(methylsulfonyl)phenoxy)-1H-pyrazolo[3,4-b]pyridin-6-yl)-1H-indazol-3-amine |
| 106 | 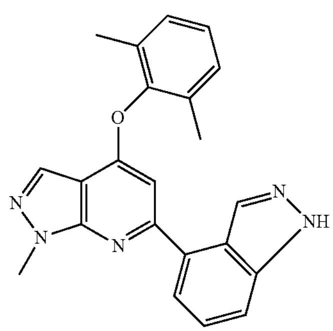 [SMILES: Cc1cccc(C)c1Oc1cc(-c2cccc3[nH]ncc23)nc2c1cnn2C] | 4-(2,6-dimethylphenoxy)-6-(1H-indazol-4-yl)-1-methyl-1H-pyrazolo[3,4-b]pyridine |
| 107 | 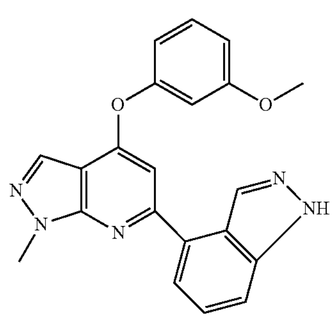 [SMILES: COc1cccc(Oc2cc(-c3cccc4[nH]ncc34)nc3c2cnn3C)c1] | 6-(1H-indazol-4-yl)-4-(3-methoxyphenoxy)-1-methyl-1H-pyrazolo[3,4-b]pyridine |

TABLE 1-continued

| No. | Structure | Name |
|---|---|---|
| 108 | 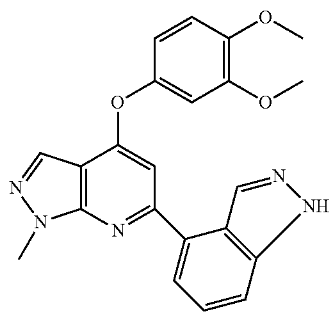 [SMILES: COc1ccc(Oc2cc(-c3cccc4[nH]ncc34)nc3c2cnn3C)cc1OC] | 4-(3,4-dimethoxyphenoxy)-6-(1H-indazol-4-yl)-1-methyl-1H-pyrazolo[3,4-b]pyridine |
| 109 | 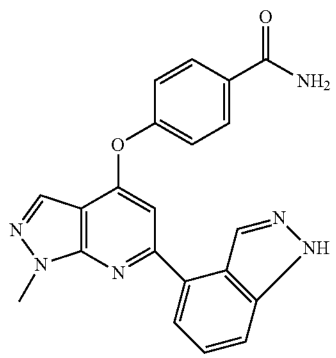 [SMILES: Cn1ncc2c(Oc3ccc(C(N)=O)cc3)cc(-c3cccc4[nH]ncc34)nc21] | 4-(6-(1H-indazol-4-yl)-1-methyl-1H-pyrazolo[3,4-b]pyridin-4-yloxy)benzamide |
| 110 | 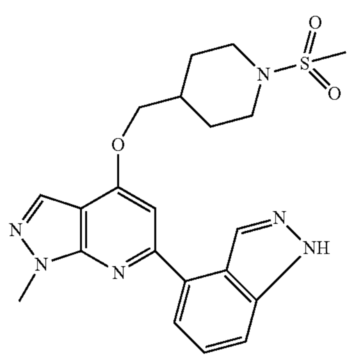 [SMILES: Cn1ncc2c(OCC3CCN(S(C)(=O)=O)CC3)cc(-c3cccc4[nH]ncc34)nc21] | 6-(1H-indazol-4-yl)-1-methyl-4-((1-(methylsulfonyl)piperidin-4-yl)methoxy)-1H-pyrazol[3,4-b]pyridine |
| 111 | 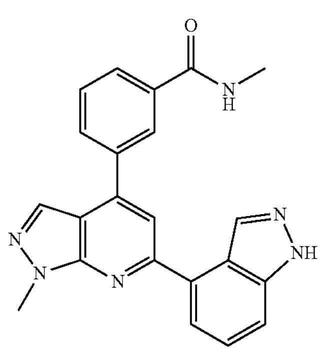 [SMILES: CNC(=O)c1cccc(-c2cc(-c3cccc4[nH]ncc34)nc3c2cnn3C)c1] | 3-(6-(1H-indazol-4-yl)-1-methyl-1H-pyrazolo[3,4-b]pyridine-4-yl)-N-methylbenzamide |

TABLE 1-continued

| No. | Structure | Name |
|---|---|---|
| 112 | 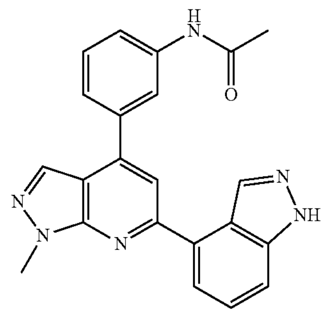 [SMILES: CC(=O)Nc1cccc(-c2cc(-c3cccc4[nH]ncc34)nc3c2cnn3C)c1] | N-(3-(6-(1H-indazol-4-yl)-1-methyl-1H-pyrazolo[3,4-b]pyridin-4-yl)phenyl)acetamide |
| 113 | 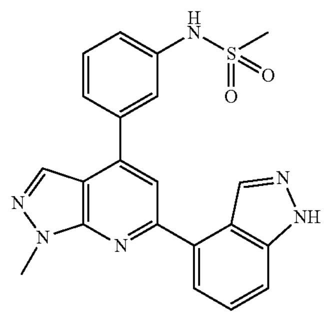 [SMILES: Cn1ncc2c(-c3cccc(NS(C)(=O)=O)c3)cc(-c3cccc4[nH]ncc34)nc21] | N-(3-(6-(1H-indazol-4-yl)-1-methyl-1H-pyrazolo[3,4-b]pyridin-4-yl)phenyl)methanesulfonamide |
| 114 | 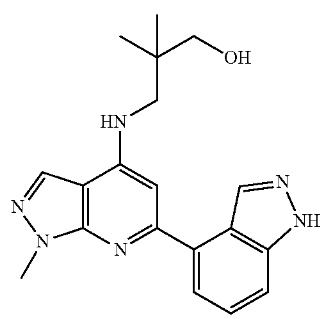 [SMILES: Cn1ncc2c(NCC(C)(C)CO)cc(-c3cccc4[nH]ncc34)nc21] | 3-(6-(1H-indazol-4-yl)-1-methyl-1H-pyrazolo[3,4-b]pyridin-4-ylamino)-2,2-dimethylpropan-1-ol |
| 115 | 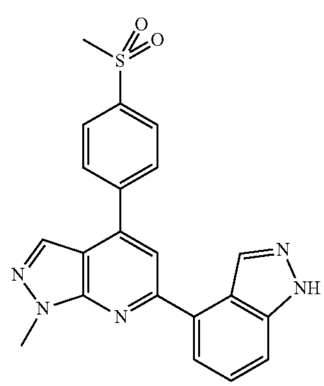 [SMILES: Cn1ncc2c(-c3ccc(S(C)(=O)=O)cc3)cc(-c3cccc4[nH]ncc34)nc21] | 6-(1H-indazol-4-yl)-1-methyl-4-(4-(methylsulfonyl)phenyl)-1H-pyrazolo[3,4-b]pyridine |

TABLE 1-continued

| No. | Structure | Name |
|---|---|---|
| 116 | 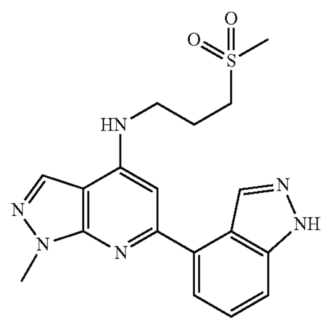 [SMILES: Cn1ncc2c(NCCCS(C)(=O)=O)cc(-c3cccc4[nH]ncc34)nc21] | 6-(1H-indazol-4-yl)-1-methyl-N-(3-(methylsulfonyl)propyl)-1H-pyrazolo[3,4-b]pyridin-4-amine |
| 117 | 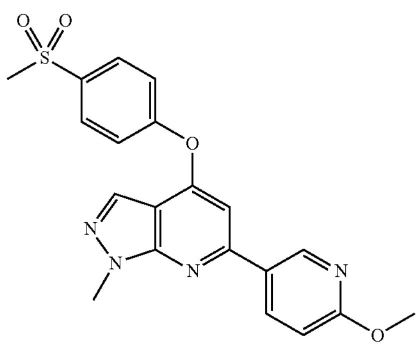 | 6-(6-methoxypyridin-3-yl)-1-methyl-4-(4-(methylsulfonyl)phenoxy)-1H-pyrazolo[3,4-b]pyridine |
| 118 | 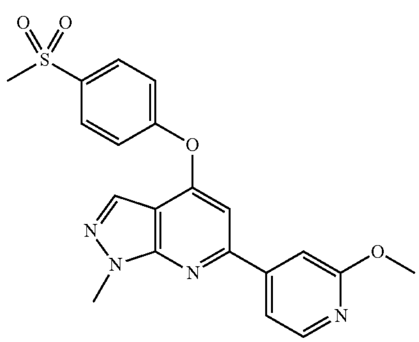 | 6-(2-methoxypyridin-4-yl)-1-methyl-4-(4-(methylsulfonyl)phenoxy)-1H-pyrazolo[3,4-b]pyridine |
| 119 | 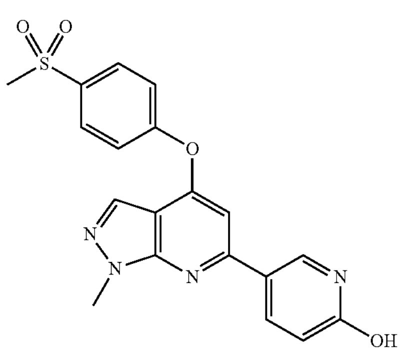 [SMILES: Cn1ncc2c(Oc3ccc(S(C)(=O)=O)cc3)cc(-c3ccc(O)nc3)nc21] | 5-(1-methyl-4-(4-(methylsulfonyl)phenoxy)-1H-pyrazolo[3,4-b]pyridin-6-yl)pyridin-2-ol |

TABLE 1-continued

| No. | Structure | Name |
|---|---|---|
| 120 | 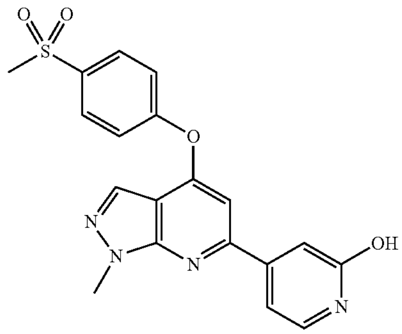 [SMILES: Cn1ncc2c(Oc3ccc(S(C)(=O)=O)cc3)cc(-c3ccnc(O)c3)nc21] | 4-(1-methyl-4-(4-(methylsulfonyl)phenoxy)-1H-pyrazolo[3,4-b]pyridin-6-yl)pyridin-2-ol |
| 121 | | 7-(1-methyl-4-(4-(methylsulfonyl)phenoxy)-1H-pyrazolo[3,4-b]pyridin-6-yl)benzo[d]isoxazol-3-amine | format, making it amenable to automated high-throughput screening (HTS) (Cree et al (1995) Anti Cancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay an be used with various multiwell formats, e.g. 96 or 384 well format. Data can be recorded by luminometer or CCD camera imaging device. The luminescence output is presented as relative light units (RLU), measured over time.

The anti-proliferative effects of Formula I exemplary compounds were measured by the CellTiter-Glo® Assay (Example 33) against several tumor cell lines, including PC3, Detroit 562, and MDAMB361.1. $EC_{50}$ values were established for the tested compounds. The range of in vitro cell potency activities was about 100 nM to about 10 µM.

Certain ADME properties were measured for certain exemplary compounds by assays including: Caco-2 Permeability (Example 34), Hepatocyte Clearance (Example 35), Cytochrome P450 Inhibition (Example 36), Cytochrome P450 Induction (Example 37), Plasma Protein Binding (Example 38), and hERG channel blockage (Example 39).

Exemplary Formula I compounds No. 101-121 in Table 1, were made, characterized, and tested for PI3K activity according to the methods of this invention, and have the following structures and corresponding names (ChemDraw Ultra, Version 9.0.1, CambridgeSoft Corp., Cambridge Mass.). For example, compound 101 had an $IC_{50}$ of 0.0064 micromole; compound 102 had an $IC_{50}$ of 0.224 micromole; compound 103 had an $IC_{50}$ of 0.0828 micromole; compound 104 had an $IC_{50}$ of 0.00223 micromole; compound 105 had an $IC_{50}$ of 0.0137 micromole; compound 106 had an $IC_{50}$ of 0.399 micromole; compound 107

Administration of Compounds of Formula I

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Compounds of the present invention are useful for treating hyperproliferative diseases, conditions and/or disorders including, but not limited to, those characterized by over expression of lipid kinases, e.g. PI3 kinase, also known as PI3K. Accordingly, another aspect of this invention includes methods of treating or preventing diseases or conditions that can be treated or prevented by inhibiting lipid kinases, including PI3. In one embodiment, the method comprises administering to a mammal in need thereof a therapeutically effective amount of a compound of Formula I. In one embodiment, a human patient is treated with a compound of Formula I and a pharmaceutically acceptable carrier, adjuvant, or vehicle, wherein said compound of Formula I is present in an amount to detectably inhibit PI3 kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Another aspect of this invention provides a compound of this invention for use in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e. an alcohol having two or more hydroxyl groups, such as propylene glycol, butane 1,3-diol, mannitol, sorbitol, glycerol and polyethylene glycol (including PEG 400) and mixtures thereof. The topical formulations may include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or an oil, or with both a fat and an oil. A hydrophilic emulsifier may be included together with a lipophilic emulsifier which acts as a stabilizer. It is also preferred to include an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as a hyperproliferative disorder (e.g., cancer). In certain embodiments, a compound of Formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, geometric isomer, tautomer, solvate, metabolite, or pharmaceutically acceptable salt or prodrug thereof, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula I, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method. The amounts of the compound(s) of Formula I and the other pharmaceutically active chemotherapeutic agent(s) and the relative timings of administration will be selected in order to achieve the desired combined therapeutic effect.

Metabolites of Compounds of Formula I

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I, or a stereoisomer, geometric isomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

EXAMPLES

The chemical reactions described in the Examples may be readily adapted to prepare a number of other PI3K inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated all temperatures are set forth in degrees Celsius. Reagents were purchased from commercial suppliers such as Sigma Aldrich Chemical Company, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters). $^1$H NMR spectra were obtained at 400 MHz in deuterated CDCl$_3$, d$_6$-DMSO, CH$_3$OD or d$_6$-acetone solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

Ethyl 4-hydroxy-1-methyl-6-oxo-6,7-dihydro-1H-pyrazolo[3,4-b]pyridine-5-carboxylate 3

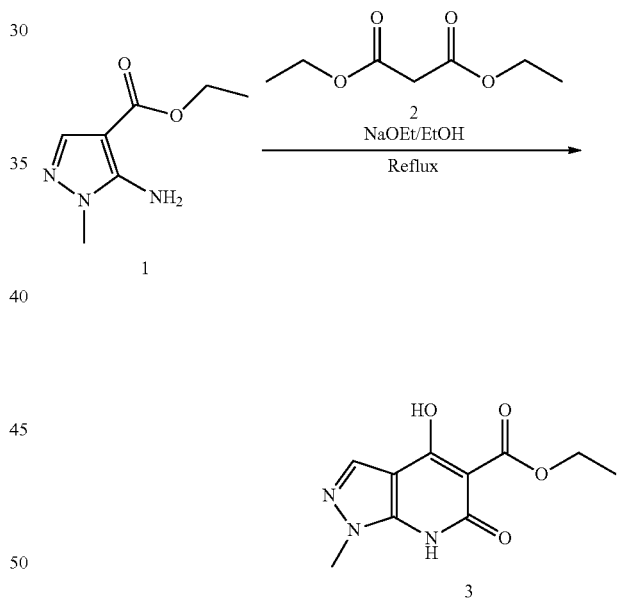

Sodium ethoxide (95%, 83 g, 1.18 moles) was dissolved in 175 mL of absolute ethanol, following the protocol described in *J. Heterocyclic Chem.* (1978) 15:319 with some modifications. Diethylmalonate 2 (184.6 g, 1.18 moles) was added and stirred at room temperature for 10 minutes. Ethyl 5-amino-1-methylpyrazole-4-carboxylate 1 (50 g, 0.295 moles) was added slowly and the resulting solution refluxed overnight at 100° C. During the reflux period, an off-white solid began to form. The solution was evaporated to dryness on a rotary evaporator and the residue dissolved in a minimum amount of water. Upon acidification (pH 2) of the aqueous solution with concentrated hydrochloric acid, the resulting precipitate was filtered and recrystallized from acetic acid-water to give 3 as a white solid (~45 g, 64%). NMR (trifluoroacetic acid): δ 1.60

(t.3H.J=7 Hz, CH3 of ester), 4.22 (s, 3H, N—CH₃), 4.80 (q, 2H, J=7 hz, CH₂), 8.49 (s, 1H, H-3)

Example 2

4-Hydroxy-1-methyl-1H-pyrazolo[3,4-b]pyridine-6(7H)-one 4

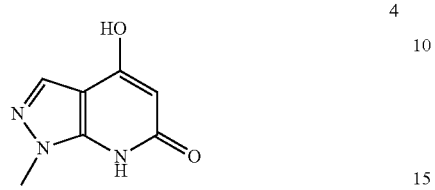

4

Following the protocol described in *J. Heterocyclic Chem.* (1978) 15:319, 45 g (0.189 moles) of ethyl 4-hydroxy-1-methyl-6-oxo-6,7-dihydro-1H-pyrazolo[3,4-b]pyridine-5-carboxylate 3 was dissolved in 500 mL of 15% sodium hydroxide solution, refluxed for 5.5 hours, cooled to room temperature and placed in an ice bath. Upon acidification to pH 3 with concentrated hydrochloric acid, the precipitate which resulted was isolated by filtration and recrystallized from water to obtain 4 as a white solid (29.3 g, 94%). NMR (trifluoroacetic acid): δ 4.20 (s, 3H, CH3), 6.41 (s, 1H, H-5), 8.48 (s, 1H, H-3)

Example 3

4,6-Dichloro-1-methyl-1H-pyrazolo[3,4-b]pyridine 5

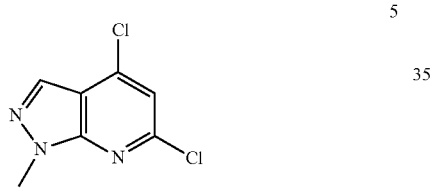

5

Phenylphosphonic acid (28.3 g, 145.32 mmol) was added to 4-hydroxy-1-methyl-1H-pyrazolo[3,4-b]pyridine-6(7H)-one 4 (4.0 g, 24.22 mmol) and the resulting mixture was heated at 170° C. overnight under nitrogen. The reaction mixture was slowly poured into crushed ice and stirred vigorously. Ammonium hydroxide was then added carefully to adjust the pH to about 5. The white precipitate formed was collected by filtration, washed with water and dried to give 5 (3.67 g, 75%). ¹H NMR (400 MHz, DMSO) δ 8.28 (s, 1H), 7.55 (s, 1H), 4.04 (s, 3H). MS (ESI) m/z 202.0 (M+1)⁺

Example 4

4-Chloro-6-(1H-indazol-4-yl)-1-methyl-1H-pyrazolo[3,4-b]pyridine 7

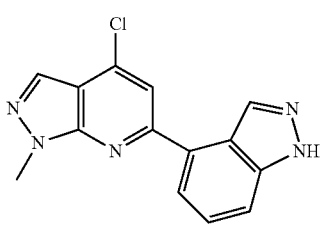

7

4,6-Dichloro-1-methyl-1H-pyrazolo[3,4-b]pyridine 5 (1.0 g, 4.94 mmol) was dissolved in 2 mL dioxane and 2 mL acetonitrile in a microwave tube, and nitrogen was bubbled through the solution. 4-(4,4,5,5-Tetramethyl-[1,3,2]dioxaborolan-2-yl)-1H-indazole 6, (1.8 g, 7.42 mmol) was added.

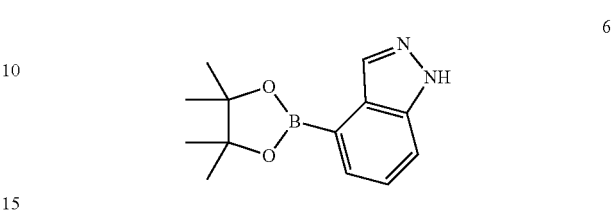

6

A solution of sodium bicarbonate (1.57 g, 14.84 mmol) in 6 mL water and nitrogen was bubbled through the mixture followed by the addition of 5 mole % of dichloro,bis(triphenylphosphine) palladium (II). The resultant mixture was then heated by microwave at 150° C. for 30 minutes. Water was added to the reaction mixture and the resulting precipitate was collected, dried, and purified by flash chromatography (methanol/DCM) to give 7 (0.930 g, 66%). ¹H NMR (400 MHz, DMSO) δ 13.29 (s, 1H), 8.87 (s, 1H), 8.49-6.59 (m, 6H), 4.13-(m, 3H). MS (ESI) m/z 284.2 (M+1)⁺

Example 5

5-(4,4,5,5-tetramethyl-1,3,2-dioxaborolan-2-yl)-1H-indazole 11

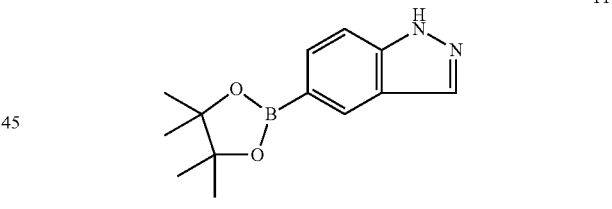

11

Potassium acetate (0.44 g, 4.5 mmol) was added to a solution of 5-bromo-1H-indazole 10 (0.1 g, 0.5 mmol) and bis (pinacolato)diboron (0.38 g, 1.52 mmol) in DMSO. Nitrogengas was bubbled through followed by the addition of 3 mole % of dichloro 1,1'-bis(diphenyl phosphino)ferrocene palladium II (Pd(dppf)Cl₂) and the reaction mixture was heated at 150° C. in a microwave for 30 minutes. The solvent was removed, and the residue was taken up into ethyl acetate and filtered through celite. The organic portions were washed with water and dried over anhydrous magnesium sulfate and the solvent was removed under reduced pressure. The crude material obtained was then purified using silica gel chromatography using hexane and ethyl acetate as eluent to give 11.

Example 6

4-chloro-6-(1H-indazol-5-yl)-1-methyl-1H-pyrazolo[3,4-b]pyridine 12

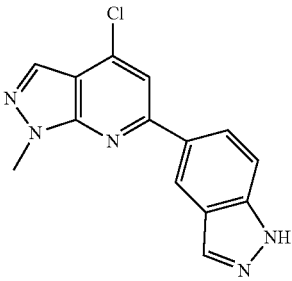

12

4,6-Dichloro-1-methyl-1H-pyrazolo[3,4-b]pyridine 5 (0.180 g, 0.89 mmol) was dissolved in 2 mL dioxane and 2 mL acetonitriile in a microwave tube, and nitrogen was bubbled through the solution. 5-(4,4,5,5-Tetramethyl-1,3,2-dioxaborolan-2-yl)-1H-indazole (0.217 g, 0.89 mmol) and a 1M solution of potassium acetate (2 mL, 2 mmol) were added. Nitrogen gas was bubbled through the mixture followed by the addition of 5 mole % of tetrakis(triphenylphosphine) palladium (0). The resultant mixture was microwaved at 125° C. for 30 minutes. Purification via Biotage reverse phase system (4:1 ethyl acetate/hexanes) gave 12.

Example 7

3-(4-Chloro-1-methyl-1H-pyrazolo[3,4-b]pyridin-6-yl)-2-fluorobenzonitrile 15

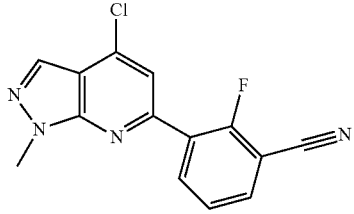

15

Potassium acetate (4 mL, 1M, 4 mmol) was added to a mixture of 4,6-dichloro-1-methyl-1H-pyrazolo[3,4-b]pyridine 5 (0.115 g, 0.569 mmol), 3-cyano-2-fluorophenylboronic acid 14 (0.075 g, 0.455 mmol) in DMF (2 mL) and acetonitrile (2 mL). Nitrogen was bubbled through the mixture followed by the addition of 10 mole % tetrakis(triphenylphosphine) palladium (0) and the reaction was heated at 125° C. in a microwave for 20 minutes. Solvent was removed, and the residue was dissolved in ethyl acetate and washed with saturated sodium bicarbonate solution and brine (15 mL). The organic portions were pooled and dried over anhydrous sodium sulfate and the solvent was removed. The crude material was purified by reverse phase chromatography (Biotage) using ethyl acetate and hexanes as solvents to give 15 as white solid (0.035 g, 20%)

Example 8

7-(4-Chloro-1-methyl-1H-pyrazolo[3,4-b]pyridin-6-yl)-1H-indazol-3-amine 16

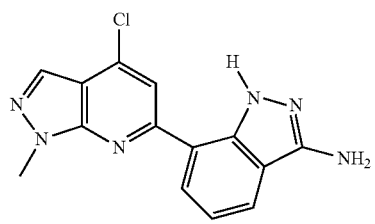

16

Hydrazine (0.34 mL, 1.04 mmol) was added to a solution of 3-(4-chloro-1-methyl-1H-pyrazolo[3,4-b]pyridin-6-yl)-2-fluorobenzonitrile 15 (0.030 g, 0.1046 mmol) in n-butanol and the reaction mixture was heated at 90° C. for 1 hour. The solvent was removed and diluted with ethylacetate, washed with saturated bicarbonate solution followed by brine. Drying and concentration gave 16.

Example 9

7-(4-Chloro-1-methyl-1H-pyrazolo[3,4-b]pyridin-6-yl)benzo[d]isoxazol-3-amine 17

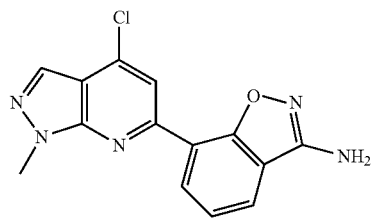

17

3-(4-Chloro-1-methyl-1H-pyrazolo[3,4-b]pyridin-6-yl)-2-fluorobenzonitrile 15 (90 mg, 0.299 mmol) was added to a mixture of acetohydroxamic acid, $CH_3C(O)NHOH$ (0.0675 g, 0.899 mmol) and potassium carbonate (0.145 g, 1.049 mmol) in 4 mL dimethylformamide and the resultant reaction mixture was heated for 2 hours at 50° C. The solvent was removed, diluted with ethyl acetate and washed with saturated sodium bicarbonate (1×20 mL) followed by brine (1×20 mL), dried over anhydrous sodium sulfate, concentrated and purified by a Biotage purification system eluting with ethyl acetate and hexanes to obtain 17 (35 mg, 40%).

Example 10

(1-(Methylsulfonyl)piperidin-4-yl)methanol 19

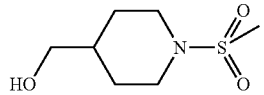

Ethyl 1-(methylsulfonyl)piperidine-4-carboxylate 18 was reacted with lithium aluminum hydride in THF to give 19.

Example 11

6-(1H-indazol-4-yl)-1-methyl-4-(4-(methylsulfonyl)phenoxy)-1H-pyrazolo[3,4-b]pyridine 101

4-Chloro-6-(1H-indazol-4-yl)-1-methyl-1H-pyrazolo[3,4-b]pyridine 7 (0.1 g, 0.352 m moles) was dissolved in 2 mL DMF. 4-Methylsulfonylphenol 8a (0.12 g, 0.704 mmol) and potassium carbonate (0.24 g, 1.76 mmol) were added. After bubbling nitrogen gas through the reaction mixture, it was heated by microwave at 155° C. for 1.5-2 hours. Solvent was removed, excess potassium carbonate was filtered and partitioned and extracted with ethyl acetate. The organic portions were washed with saturated sodium bicarbonate solution followed by brine, dried over anhydrous $Na_2SO_4$, solvent removed and purified to obtain 101. $^1$H NMR (400 MHz, DMSO) δ 13.26 (s, 1H), 8.77 (s, 1H), 8.06 (d, J=8.8, 2H), 7.92-7.51 (m, 6H), 7.51-7.27 (m, 2H), 4.13 (s, 3H), 3.28 (s, 3H) MS (ESI) m/z 420.1 (M+1)$^+$

Example 12

6-(1H-indazol-5-yl)-1-methyl-4-(4-(methylsulfonyl)phenoxy)-1H-pyrazolo[3,4-b]pyridine 102

Potassium carbonate (0.77 g, 5.36 mmol) was added to 4-chloro-6-(1H-indazol-4-yl)-1-methyl-1H-pyrazolo[3,4-b]pyridine 7 (0.16 g, 0.563 mmol) and 4-methylsulfonyl phenol 8a (0.15 g, 0.9 mmol) in dimethyl formamide. Nitrogen was bubbled through the reaction mixture which was heated in the microwave at 155° C. for 1 h. Solvent was removed and the residue was taken into ethyl acetate and washed with saturated bicarbonate followed by brine and dried over anhydrous sodium sulfate. Solvent was removed and the crude product was purified using mass directed purification to obtain 102 (32 mg, 14%)

Example 13

6-(1H-indazol-4-yl)-1-methyl-N-propyl-1H-pyrazolo[3,4-b]pyridin-4-amine 103

A solution of 4-Chloro-6-(1H-indazol-4-yl)-1-methyl-1H-pyrazolo[3,4-b]pyridine 7 (0.04 g, 0.14 mmol) in acetonitrile (2 mL) was treated with propylamine (0.041 g, 0.7 mmol) in the presence of p-toluenesulfonic acid monohydrate (0.03 g, 0.14 mmol). The reaction mixture was heated at 190° C. in microwave for 2 h. Solvent were removed and the crude material was purified by mass directed purification to obtain 5 mg of 103 as a white solid. $^1$H NMR (400 MHz, MeOD) δ 8.57 (s, 1H), 8.11 (d, J=1.2, 1H), 7.63 (t, J=7.4, 2H), 7.50 (t, J=7.2, 1H), 6.72 (s, 1H), 4.04 (t, J=22.1, 3H), 3.40 (dd, J=20.2, 13.0, 2H), 1.79 (dd, J=14.5, 7.1, 2H), 1.07 (t, J=7.4, 3H). MS (ESI) m/z 307.2 (M+1)$^+$

Example 14

6-(1H-indazol-4-yl)-1-methyl-N-(4-(methylsulfonyl)phenyl)-1H-pyrazolo[3,4-b]pyridin-4-amine 104

A solution of 4-chloro-6-(1H-indazol-4-yl)-1-methyl-1H-pyrazolo[3,4-b]pyridine 7 (0.04 g, 0.14 mmol) in dioxane was treated with 4-methylsulphonylaniline hydrochloride (0.058 g, 0.28 mmol) in the presence of (tris(dibenzylidene acetone) dipalladium(0), $Pd_2(dba)_3$ (0.13 g, 0.014 mmol), XANPHOS (0.016 g, 0.028 mmol) and cesium carbonate (0.18 g, 0.56 mmol) and the reaction mixture were heated overnight at 100° C. The reaction mixture was diluted with ethylacetate and water. The aqueous portions were extracted with ethyl acetate and the organic portions pooled and dried over anhydrous sodium sulfate. The solvent were removed and the crude material purified (Biotage) to obtain 10 mg of 104. $^1$H NMR (400 MHz, MeOD) δ 8.69 (s, 1H), 8.12 (s, 1H), 7.97 (d, J=8.7, 2H), 7.78-7.55 (m, 4H), 7.59-7.44 (m, 2H), 4.17 (s, 3H), 3.35 (s, 1H), 3.14 (s, 3H). MS (ESI) m/z 419.2 (M+1)$^+$

Example 15

7-(1-methyl-4-(4-(methylsulfonyl)phenoxy)-1H-pyrazolo[3,4-b]pyridin-6-yl)-1H-indazol-3-amine 105

Potassium carbonate (0.14 g, 1.04 mmol) was added to a solution of 7-(4-chloro-1-methyl-1H-pyrazolo[3,4-b]pyridin-6-yl)-1H-indazol-3-amine 16 (0.30 g, 0.1046 mmol) and 4-methylsulfonyl phenol 8a (0.036 g, 0.2 mmol) in 2 mL DMF. Nitrogen was bubbled through the solution. The reaction mixture was heated in a microwave at 155° C. for 40 minutes. The crude compound was purified by mass directed purification to obtain 20 mg, 40% of 105 as a yellow solid. $^1$H NMR (400 MHz, DMSO) δ 11.53 (s, 1H), 8.21-7.64 (m, 6H), 7.64-7.40 (m, 3H), 7.40-6.91 (m, 1H), 5.51 (s, 2H), 4.12 (m, 3H), 3.21 (m, 3H). MS (ESI) m/z 435.1 (M+1)$^+$

Example 16

4-(2,6-dimethylphenoxy)-6-(1H-indazol-4-yl)-1-methyl-1H-pyrazolo[3,4-b]pyridine 106

4-Chloro-6-(1H-indazol-4-yl)-1-methyl-1H-pyrazolo[3,4-b]pyridine 7 (0.040 g, 0.141 mmol) was dissolved in 2 mL DMF. 2,6-Dimethylphenol 8b (0.034 g, 0.281 mmol) was added followed by the addition of potassium carbonate (0.2 g, 1.41 mmol) and the resultant reaction mixture was heated in a microwave at 155° C. for 30 minutes. The reaction mixture was diluted with ethyl acetate and filtered and the organic portions were washed with saturated sodium bicarbonate solution followed by brine, dried over anhydrous sodium sulfate and solvent removed and purified to obtain 106 as a white solid (10 mg, 20%). $^1$H NMR (400 MHz, CDCl$_3$) δ 10.13 (s, 1H), 8.77 (s, 1H), 7.58 (t, J=7.2, 2H), 7.48 (dd, J=11.8, 19.0, 2H), 7.18 (s, 3H), 6.97 (d, J=23.8, 1H), 4.22 (s, 3H), 2.19 (s, 6H)

Example 17

6-(1H-indazol-4-yl)-4-(3-methoxyphenoxy)-1-methyl-1H-pyrazolo[3,4-b]pyridine 107

4-Chloro-6-(1H-indazol-4-yl)-1-methyl-1H-pyrazolo[3,4-b]pyridine 7 (0.040 g, 0.141 mmoles) was dissolved in 2 mL DMF. 3-Methoxyphenol 8e (0.033 g, 0.282 mmol) was added followed by the addition of potassium carbonate (0.2 g, 1.41 mmol). Nitrogen was bubbled through the resultant reaction mixture and heated in a microwave at 155° C. for 1 hour. The reaction mixture was diluted with ethyl acetate and filtered and the organic portions were washed with saturated sodium bicarbonate solution followed by brine, dried over anhydrous sodium sulfate, solvent removed, and purified to obtain the desired product which was to obtain 107 as a white solid (15.0 mg, 30%)

Example 18

4-(3,4-dimethoxyphenoxy)-6-(1H-indazol-4-yl)-1-methyl-1H-pyrazolo[3,4-b]pyridine 108

4-Chloro-6-(1H-indazol-4-yl)-1-methyl-1H-pyrazolo[3,4-b]pyridine 7 (0.040 g, 0.141 mmoles) was dissolved in 2 mL DMF. 3,4-Dimethoxyphenol 8c (0.035 g, 0.281 mmol) was added followed by the addition of potassium carbonate (0.2 g, 1.41 mmol) and the resultant reaction mixture was heated in a microwave at 155° C. for 1 hour. The reaction mixture was diluted with ethyl acetate and filtered. The organic portions were washed with saturated sodium bicarbonate solution followed by brine, dried over anhydrous sodium sulfate, solvent removed and purified to obtain 108 as a white solid (10 mg, 20%). $^1$H NMR (400 MHz, CDCl$_3$) δ 10.13 (s, 1H), 8.81 (s, 1H), 7.76-7.40 (m, 4H), 7.14-6.87 (m, 2H), 6.87-6.65 (m, 2H), 4.25 (d, J=16.2, 3H), 3.91 (d, J=31.0, 6H) MS (ESI) m/z 402.2 (M+1)$^+$

Example 19

4-(6-(1H-indazol-4-yl)-1-methyl-1H-pyrazolo[3,4-b]pyridin-4-yloxy)benzamide 109

4-Chloro-6-(1H-indazol-4-yl)-1-methyl-1H-pyrazolo[3,4-b]pyridine 7 (0.040 g, 0.141 mmoles) was dissolved in 2 mL DMF. 4-Hydroxybenzamide 8d (0.038 g, 0.281 mmol) was added followed by the addition of potassium carbonate (0.2 g, 1.41 mmol) and the resultant reaction mixture was heated in a microwave at 155° C. for 1 hour. The reaction mixture was diluted with ethyl acetate and filtered and the organic portions were washed with saturated sodium bicarbonate solution followed by brine, dried over anhydrous sodium sulfate, solvent removed and purified to obtain 109 as a white solid (10 mg, 20%). $^1$H NMR (400 MHz, DMSO) δ 13.25 (s, 1H), 8.72 (s, 1H), 8.04 (d, J=8.7, 3H), 7.83-7.59 (m, 3H), 7.59-7.29 (m, 4H), 7.23 (s, 1H), 4.16 (d, J=9.1, 3H). MS (ESI) m/z 385.1 (M+1)$^+$

Example 20

6-(1H-indazol-4-yl)-1-methyl-44(1-(methylsulfonyl)piperidin-4-yl)methoxy)-1H-pyrazolo[3,4-b]pyridine 110

(1-(Methylsulfonyl)piperidin-4-yl)methanol 19 (0.367 g, 1.9 mmol) was added to a mixture of sodium hydride (0.137 g, 5.70 mmol) in DMF and stirred for 2 hours at ambient temperature. 4-Chloro-6-(1H-indazol-4-yl)-1-methyl-1H-pyrazolo[3,4-b]pyridine 7 (0.18 g, 0.634 mmol) in 10 mL DMF was added slowly to the mixture and stirred at 80° C. overnight. The reaction mixture was quenched onto crushed ice and extracted with ethyl acetate. The organic portions were pooled and dried over anhydrous sodium sulfate and solvent was removed under reduced pressure. The crude material was purified to obtain 110 (70 mg, 25%). $^1$H NMR (400 MHz, DMSO) δ 13.22 (s, 1H), 8.82 (s, 1H), 8.15 (s, 1H), 7.86 (d, J=7.1, 1H), 7.67 (d, J=8.3, 1H), 7.58-7.41 (m, 1H), 7.35 (s, 1H), 4.36 (d, J=6.3, 2H), 4.13 (s, 3H), 3.63 (d, J=11.8, 2H), 3.04-2.61 (m, 4H), 2.22-1.78 (m, 4H), 1.45 (d, J=8.6, 2H). MS (ESI) m/z 441.2 (M+1)$^+$

Example 21

3-(6-(1H-indazol-4-yl)-1-methyl-1H-pyrazolo[3,4-b]pyridin-4-yl)-N-methylbenzamide 111

4-Chloro-6-(1H-indazol-4-yl)-1-methyl-1H-pyrazolo[3,4-b]pyridine 7 (80 mg, 0.28 mmol) and 3-(N-methylaminocarbonyl)phenyl boronic acid (1.4 equiv.) were suspended in 2 ml acetonitrile. Sodium carbonate (3 equiv., 92 mg) and bis(triphenylphosphine)palladium(II) chloride (0.05 equiv.) were added as a solution in water (0.5 ml). The reaction mixture was heated in microwave at 130° C. for 20 min. Water was added to the mixture, and the precipitated product was filtered and purified by column chromatography to yield 111. NMR (CDCl$_3$): 3.11 (3H, d), 4.34 (3H, s), 6.25 (1H, br), 7.56 (1H, m), 7.63-7.70 (2H, m), 7.84 (1H, d), 7.87 (1H, s), 7.90 (1H, d), 8.00 (1H, d), 8.21 (1H, s), 8.27 (1H, s), 8.97 (1H, s). MS: MH+ 383.09 (100%)

Example 22

N-(3-(6-(1H-indazol-4-yl)-1-methyl-1H-pyrazolo[3,4-b]pyridin-4-yl)phenyl)acetamide 112

4-Chloro-6-(1H-indazol-4-yl)-1-methyl-1H-pyrazolo[3,4-b]pyridine 7 (80 mg, 0.28 mmol) and 3'-(4,4,5,5-tetramethyl-1,3,2-dioxaborolan-2-yl)acetanilide (1.4 equiv.) were suspended in 2 ml acetonitrile. Sodium carbonate (3 equiv., 92 mg) and bis(triphenylphosphine)palladium(II) chloride (0.05 equiv.) were added as a solution in water (0.5 ml). The reaction mixture was heated in microwave at 130° C. for 20 min. Water was added to the mixture, and the precipitated product was filtered and purified by column chromatography to yield 112. NMR (CDCl$_3$): 2.27 (3H, s), 4.33 (3H, s), 7.34 (1H, br), 7.52-7.68 (5H, m), 7.84 (1H, d), 7.85 (1H, s), 8.10 (1H, s), 8.26 (1H, s), 8.96 (1H, s). MS: MH+ 383.12 (100%)

Example 23

N-(3-(6-(1H-indazol-4-yl)-1-methyl-1H-pyrazolo[3,4-b]pyridin-4-yl)phenyl)methanesulfonamide 113

4-Chloro-6-(1H-indazol-4-yl)-1-methyl-1H-pyrazolo[3,4-b]pyridine 7 (80 mg, 0.28 mmol) and N-3-(4,4,5,5-tetramethyl-1,3,2-dioxaborolan-2-yl)phenyl methanesulfonamide (1.4 equiv.) were suspended in 2 ml acetonitrile. Sodium carbonate (3 equiv., 92 mg) and bis(triphenylphosphine)palladium(II) chloride (0.05 equiv.) were added as a solution in water (0.5 ml). The reaction mixture was heated in microwave at 130° C. for 20 min. Water was added to the mixture, and the precipitated product was filtered and purified by column chromatography to yield 113. NMR (CDCl$_3$): 3.14 (3H, s), 4.34 (3H, s), 6.75 (1H, br), 7.39 (1H, dd), 7.54-7.71 (4H, m), 7.74 (1H, s), 7.82-7.84 (2H, m), 8.22 (1H, s), 8.95 (1H, s), 10.20 (1H, br). MS: MH+ 418.12

Example 24

3-(6-(1H-indazol-4-yl)-1-methyl-1H-pyrazolo[3,4-b]pyridin-4-ylamino)-2,2-dimethylpropan-1-ol 114

4-Chloro-6-(1H-indazol-4-yl)-1-methyl-1H-pyrazolo[3,4-b]pyridine 7 (70 mg) and 3-amino-2,2-dimethyl-1-propanol (3 equiv.) were heated in microwave at 170° C. for two hours. Volatiles were removed in vacuo; the residue was purified by prep HPLC to give 114 as a white solid (55 mg). NMR (CDCl$_3$): 1.11 (6H, s), 1.72 (1H, br, OH), 3.42 (2H, d), 3.64 (2H, d), 4.19 (3H, s), 5.70 (1H, br, NH), 6.78 (1H, s), 7.49-7.58 (2H, m), 7.71 (1H, d), 7.94 (1H, s), 8.82 (1H, s), 10.10 (1H, br, NH). MS: MH+ 351

Example 25

6-(1H-indazol-4-yl)-1-methyl-4-(4-(methylsulfonyl)phenyl)-1H-pyrazolo[3,4-b]pyridine 115

4-Chloro-6-(1H-indazol-4-yl)-1-methyl-1H-pyrazolo[3,4-b]pyridine 7 (80 mg, 0.28 mmol) and 4-(methanesulfonyl)benzene boronic acid (1.4 equiv.) were suspended in 2 ml acetonitrile. Sodium carbonate (3 equiv., 92 mg) and bis(triphenylphosphine)palladium(II) chloride (0.05 equiv.) were added as a solution in water (0.5 ml). The reaction mixture was heated in microwave at 130° C. for 20 min. Water was added to the mixture, and the precipitated product was filtered and purified by column chromatography to yield 115. NMR (CDCl$_3$): 3.19 (3H, s), 4.36 (3H, s), 7.58 (1H, m), 7.67 (1H, d), 7.84 (1H, d), 7.87 (1H, s), 8.06 (2H, d), 8.19 (1H, s), 8.20 (2H, d), 8.96 (1H, s), 10.20 (1H, br). MS: MH+ 404

Example 26

6-(1H-indazol-4-yl)-1-methyl-N-(3-(methylsulfonyl)propyl)-1H-pyrazolo[3,4-b]pyridin-4-amine 116

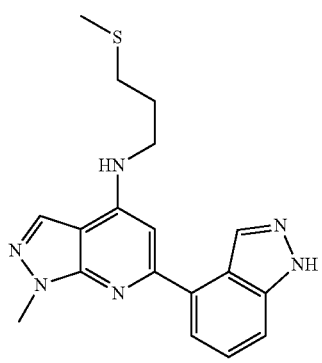 [SMILES: CSCCCNc1cc(-c2cccc3[nH]ncc23)nc2c1cnn2C]

4-Chloro-6-(1H-indazol-4-yl)-1-methyl-1H-pyrazolo[3,4-b]pyridine 7 (100 mg) and 3-(methylthio)propylamine (3 equiv.) were heated in microwave at 170° C. for one hour following General Procedure B. Volatiles were removed in vacuo; the residue was purified by prep HPLC to give [6-(1H-indazol-4-yl)-1-methyl-1H-pyrazolo[3,4-b]pyridin-4-yl]-(3-methylsulfanyl-propyl)-amine (94 mg) as a white solid. 3-Chloroperoxybenzoic acid (MCPBA, 94 mg, 2.2 equiv.) in 2 ml dry DCM was added at 0° C. The reaction mixture was allowed slowly to warm up to room temperature over 3 hours and extracted with DCM, washed with saturated aqueous sodium hydrogen carbonate and purified by flash chromatography (methanol/DCM) to give 116 (27 mg) as a white solid. NMR (CDCl$_3$): 2.39 (2H, m), 3.00 (3H, s), 3.25 (2H, t), 3.74 (2H, m), 4.20 (3H, s), 5.20 (1H, br t), 6.77 (1H, s), 7.50-7.54 (1H, m), 7.59 (1H, d), 7.70 (1H, d), 7.97 (1G=H, s), 8.82 (1H, s), 10.20 (1H, br). MS: MH+ 385.19 (100%)

Example 27

6-(6-methoxypyridin-3-yl)-1-methyl-4-(4-(methylsulfonyl)phenoxy)-1H-pyrazolo[3,4-b]pyridine 117

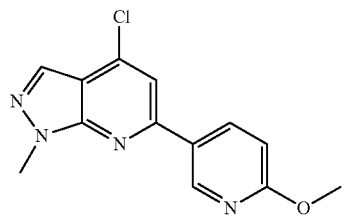 [SMILES: COc1ccc(-c2cc(Cl)c3cnn(C)c3n2)cn1]

4,6-Dichloro-1-methyl-1H-pyrazolo[3,4-b]pyridine 5 (0.5 g, 4.9 mmol) was dissolved in 1,4-dioxane (8 mL) and 6-methoxypyridin-3-ylboronic acid (0.4 g) and 1 M KOAc (8 mL) were added in a microwave tube. Nitrogen was bubbled through the solution for 1 minute. 1,1'-Bis(diphenylphosphino)ferrocenepalladium (II) chloride (1.2 g) was added and the resultant mixture was heated by microwave at 120° C. for 5 minutes. The reaction mixture was concentrated in vacuo and purified by flash chromatography (30% EtOAc in hexane) to provide 4-chloro-6-(6-methoxypyridin-3-yl)-1-methyl-1H-pyrazolo[3,4-b]pyridine (0.32 g).
To 4-chloro-6-(6-methoxypyridin-3-yl)-1-methyl-1H-pyrazolo[3,4-b]pyridine (0.32 g) and 4-(methylsulfonyl)phenol (0.40 g) in DMF (6 mL) was added potassium carbonate (0.80 g) and nitrogen was bubbled through the solution for 5 min. The reaction mixture was then heated in a microwave reactor at 150° C. for 1 h. The resulting product was purified by silica gel chromatography (0-30% EtOAc in hexane) to afford 117 (0.38 g). MS (ESI) m/z 411.1 (M+1)+

Example 28

6-(2-methoxypyridin-4-yl)-1-methyl-4-(4-(methylsulfonyl)phenoxy)-1H-pyrazolo[3,4-b]pyridine 118

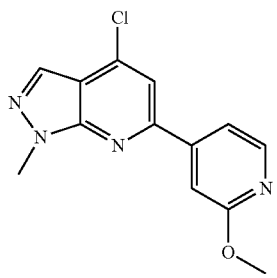 [SMILES: COc1cc(-c2cc(Cl)c3cnn(C)c3n2)ccn1]

4,6-Dichloro-1-methyl-1H-pyrazolo[3,4-b]pyridine 5 (0.5 g, 4.9 mmol) was dissolved in acetonitrile (8 mL) and 2-methoxypyridine-4-boronic acid (0.4 g) and 1 M KOAc (8 mL)

were added in a microwave tube. Nitrogen was bubbled through the solution for 5 minutes. 1,1'-Bis(diphenylphosphino)ferrocenepalladium (II) chloride (1.21 g) was added and the resultant mixture was then heated by microwave at 120° C. for 5 minutes. The reaction mixture was concentrated in vacuo and purified by flash chromatography (30% EtOAc in hexane) to provide 4-chloro-6-(2-methoxypyridin-4-yl)-1-methyl-1H-pyrazolo[3,4-b]pyridine (0.37 g).

To 4-chloro-6-(2-methoxypyridin-4-yl)-1-methyl-1H-pyrazolo[3,4-b]pyridine (0.4 g) and 4-(methylsulfonyl)phenol (0.5 g) was added DMF (3.4 mL) and potassium carbonate (1.0 g). Nitrogen was bubbled through the solution for 5 min. The reaction mixture was heated in a microwave reactor for 1 h at 150° C., then purified by reverse phase HPLC to provide 118 (0.3 g). MS (ESI) m/z 411.1 (M+1)$^+$ Example 29

5-(1-methyl-4-(4-(methylsulfonyl)phenoxy)-1H-pyrazolo[3,4-b]pyridin-6-yl)pyridin-2-ol 119

To 6-(6-methoxypyridin-3-yl)-1-methyl-4-(4-(methylsulfonyl)phenoxy)-1H-pyrazolo[3,4-b]pyridine 117 (110 mg) in acetonitrile (1 mL) was added iodotrimethylsilane (1 mL). The reaction mixture was heated at 70° C. for 3 h and purified by reverse phase HPLC to afford 119 (35.8 mg). MS (ESI) m/z 397.1 (M+1)$^+$ Example 30

4-(1-methyl-4-(4-(methylsulfonyl)phenoxy)-1H-pyrazolo[3,4-b]pyridin-6-yl)pyridin-2-ol 120

To 6-(2-methoxypyridin-4-yl)-1-methyl-4-(4-(methylsulfonyl)phenoxy)-1H-pyrazolo[3,4-b]pyridine 118 (100 mg) in acetonitrile (1 mL) was added iodotrimethylsilane (140 µl). The resulting mixture was heated 3 h at 70° C. and purified by reverse phase HPLC to provide 120. MS (ESI) m/z 397.1 (M+1)$^+$ Example 31

7-(1-methyl-4-(4-(methylsulfonyl)phenoxy)-1H-pyrazolo[3,4-b]pyridin-6-yl)benzo[d]isoxazol-3-amine 121

A mixture of 7-(4-chloro-1-methyl-1H-pyrazolo[3,4-b]pyridin-6-yl)benzo[d]isoxazol-3-amine 17 (0.032 g, 0.106 mmol), 4-methylsulfonyl phenol 8a (0.036 g, 0.213 mmol) and potassium carbonate (0.15 g, 1.06 mmol) in 2 mL DMF was heated in a microwave at 155° C. for 30 minutes. The reaction mixture was filtered, solvent removed and diluted with ethyl acetate. The organic portions were pooled and washed with saturated bicarbonate solution and brine, dried over anhydrous sodium sulfate and solvent was removed. The crude material was purified using mass directed purification to give 10 mg of 121. $^1$H NMR (400 MHz, DMSO) δ=8.02-7.58 (m, 8H), 7.58 (dd, J=26.9, 35.7, 2H), 6.53 (s, 1H), 4.15-4.01 (m, 3H), 3.3-3.06 (m, 3H). MS (ESI) m/z 436.0 (M+1)$^+$ Example 32 p110α (alpha) PI3K Binding Assay

Binding Assays: Initial polarization experiments were performed on an Analyst HT 96-384 (Molecular Devices Corp, Sunnyvale, Calif.). Samples for fluorescence polarization affinity measurements were prepared by addition of 1:3 serial dilutions of p110 alpha PI3K (Upstate Cell Signaling Solutions, Charlottesville, Va.) starting at a final concentration of 20 ug/mL in polarization buffer (10 mM Tris pH 7.5, 50 mM NaCl, 4 mM MgCl$_2$, 0.05% Chaps, and 1 mM DTT) to 10 mM PIP$_2$ (Echelon-Inc., Salt Lake City, Utah.) final concentration. After an incubation time of 30 minutes at room temperature, the reactions were stopped by the addition of GRP-1 and PIP3-TAMRA probe (Echelon-Inc., Salt Lake City, Utah.) 100 nM and 5 nM final concentrations respectively. Read with standard cut-off filters for the rhodamine fluorophore (λex=530 nm; λem=590 nm) in 384-well black low volume Proxiplates (PerkinElmer, Wellesley, Mass.) Fluorescence polarization values were plotted as a function of the protein concentration, and the EC$_{50}$ values were obtained by fitting the data to a 4-parameter equation using KaleidaGraph software (Synergy software, Reading, Pa.). This experiment also establishes the appropriate protein concentration to use in subsequent competition experiments with inhibitors.

Inhibitor IC$_{50}$ values were determined by addition of the 0.04 mg/mL p110 alpha PI3K (final concentration) combined with PIP$_2$ (10 mM final concentration) to wells containing 1:3 serial dilutions of the antagonists in a final concentration of 25 mM ATP (Cell Signaling Technology, Inc., Danvers, Mass.) in the polarization buffer. After an incubation time of 30 minutes at room temperature, the reactions were stopped by the addition of GRP-1 and PIP3-TAMRA probe (Echelon-Inc., Salt Lake City, Utah.) 100 nM and 5 nM final concentrations respectively. Read with standard cut-off filters for the rhodamine fluorophore (λex=530 nm; λem=590 nm) in 384-well black low volume proxi plates (PerkinElmer, Wellesley, Mass.) Fluorescence polarization values were plotted as a function of the antagonist concentration, and the IC$_{50}$ values were obtained by fitting the data to a 4-parameter equation in Assay Explorer software (MDL, San Ramon, Calif.).

Alternatively, inhibition of PI3K was determined in a radiometric assay using purified, recombinant enzyme and ATP at a concentration of 1 uM. The Formula I compound was serially diluted in 100% DMSO. The kinase reaction was incubated for 1 h at room temperature, and the reaction was terminated by the addition of PBS. IC$_{50}$ values were subsequently determined using sigmoidal dose-response curve fit (variable slope).

Example 33

In Vitro Cell Proliferation Assay

Efficacy of Formula I compounds were measured by a cell proliferation assay employing the following protocol (Promega Corp. Technical Bulletin TB288; Mendoza et al (2002) Cancer Res. 62:5485-5488):

1. An aliquot of 100 nl of cell culture containing about 10$^4$ cells (PC3, Detroit562, or MDAMB361.1) in medium was deposited in each well of a 384-well, opaque-walled plate.

2. Control wells were prepared containing medium and without cells.

3. The compound was added to the experimental wells and incubated for 3-5 days.

4. The plates were equilibrated to room temperature for approximately 30 minutes.

5. A volume of CellTiter-Glo Reagent equal to the volume of cell culture medium present in each well was added.

6. The contents were mixed for 2 minutes on an orbital shaker to induce cell lysis.

7. The plate was incubated at room temperature for 10 minutes to stabilize the luminescence signal.

8. Luminescence was recorded and reported in graphs as RLU=relative luminescence units.

Alternatively, cells were seeded at optimal density in a 96 well plate and incubated for 4 days in the presence of test compound. Alamar Blue™ was subsequently added to the assay medium, and cells were incubated for 6 h before reading at 544 nm excitation, 590 nm emission. $EC_{50}$ values were calculated using a sigmoidal dose response curve fit.

The anti-proliferative effects of Formula I exemplary compounds were measured by the CellTiter-Glo® Assay against various tumor cell lines, including the following:

| Cell line | Tissue Type | Mutation Status | EC50 (μmole) 101 | EC50 (μmole) 104 | EC50 (μmole) 111 | EC50 (μmole) 113 | EC50 (μmole) 115 | EC50 (μmole) 118 |
|---|---|---|---|---|---|---|---|---|
| MDA-MB-361.1 | Breast | PI3K | 0.965 | 0.475 | 1.0 | 0.749 | 0.346 | 2.4 |
| PC3 | Prostate | PTEN | 0.881 | 2 | 2.4 | 0.561 | 0.75 | 4.9 |

Example 34

Caco-2 Permeability

Caco-2 cells are seeded onto Millipore Multiscreen plates at $1 \times 10^5$ cells/cm$^2$, and cultured for 20 days. Assessment of compound permeability is subsequently conducted. The compounds are applied to the apical surface (A) of cell monolayers and compound permeation into the basolateral (B) compartment was measured. This is performed in the reverse direction (B-A) to investigate active transport. A permeability coefficient value, $P_{app}$, for each compound, a measure of the rate of permeation of the compound across the membrane, is calculated. Compounds are grouped into low ($P_{app}</=1.0 \times 10^6$ cm/s) or high ($P_{app}>/=1.0 \times 10^6$ cm/s) absorption potential based on comparison with control compounds with established human absorption.

For assessment of a compound's ability to undergo active efflux, the ratio of basolateral (B) to apical (A) transport compared with A to B was determined. Values of B–A/A–B>/=1.0 indicate the occurrence of active cellular efflux.

Example 35

Hepatocyte Clearance

Suspensions of cryopreserved human hepatocytes are used. Incubations are performed at compound concentration of 1 mM or 3 μM at a cell density of $0.5 \times 10^6$ viable cells/mL. The final DMSO concentration in the incubation is about 0.25%. Control incubations are also performed in the absence of cells to reveal any non-enzymatic degradation. Duplicate samples (50 μL) are removed from the incubation mixture at 0, 5, 10, 20, 40 and 60 minutes (control sample at 60 minutes only) and added to MeOH—containing internal standard (100 μL)—to terminate the reaction. Tolbutamide, 7-hydroxycoumarin, and testosterone may be used as control compounds. Samples are centrifuged and the supernatants at each time point pooled for analysis by LC-MSMS. From a plot of ln peak area ratio (parent compound peak area/internal standard peak area) against time, intrinsic clearance ($CL_{int}$) is calculated as follows: $CL_{int}$ (μl/min/million cells)=V×k, where k is the elimination rate constant, obtained from the gradient of ln concentration plotted against time; V is a volume term derived from the incubation volume and is expressed as uL $10^6$ cells$^{-1}$.

Example 36

Cytochrome P450 Inhibition

Formula I compounds may be screened against CYP450 targets (1A2, 2C9, 2C19, 2D6, 3A4) at about 10 concentrations in duplicate, with a top concentration of about 100 uM. Standard inhibitors (furafylline, sulfaphenazole, tranylcypromine, quinidine, ketoconazole) may be used as controls. Plates may be read using a BMG LabTechnologies PolarStar in fluorescence mode.

Example 37

Cytochrome P450 Induction

Freshly isolated human hepatocytes from a single donor may be cultured for about 48 h prior to addition of Formula I compound at three concentrations and incubated for 72 h. Probe substrates for CYP3A4 and CYP1A2 are added for 30 minutes and 1 h before the end of the incubation. At 72 h, cells and media are removed and the extent of metabolism of each probe substrate quantified by LC-MS/MS. The experiment is controlled by using inducers of the individual P450s incubated at one concentration in triplicate.

Example 38

Plasma Protein Binding

Solutions of Formula I compound (5 um, 0.5% final DMSO concentration) are prepared in buffer and 10% plasma (v/v in buffer). A 96 well HT dialysis plate is assembled so that each well is divided in two by a semi-permeable cellulose membrane. The buffer solution is added to one side of the membrane and the plasma solution to the other side; incubations are then conducted at 37° C. over 2 h in triplicate. The cells are subsequently emptied, and the solutions for each batch of compounds are combined into two groups (plasma-free and plasma-containing) then analysed by LC-MSMS using two sets of calibration standards for plasma-free (6 points) and plasma-containing solutions (7 points). The fraction unbound value for the compound is calculated.

Example 39 hERG channel blockage

Formula I compounds are evaluated for ability to modulate rubidium efflux from HEK-294 cells stably expressing hERG potassium channels using established flux methodology. Cells are prepared in medium containing RbCl, plated into 96-well plates and grown overnight to form monolayers. The efflux experiment is initiated by aspirating the media and washing each well with 3×100 μL of pre-incubation buffer (containing low [K+]) at room temperature. Following the final aspiration, 50 μL of working stock (2×) compound is added to each well and incubated at room temperature for 10 minutes. 50 μL of stimulation buffer (containing high [K+]) is then added to each well giving the final test compound concentrations. Cell plates are then incubated at room temperature for a further 10 minutes. 80 μL of supernatant from each well is then transferred to equivalent wells of a 96-well plate and analysed via atomic emission spectroscopy. The compound is screened as 10 pt duplicate $IC_{50}$ curves, n=2, from a top concentration of 100 μM.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A compound selected from Formula I:

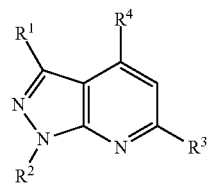

and stereoisomers, geometric isomers, tautomers, or pharmaceutically acceptable salts thereof, wherein:

$R^1$ is selected from H, $C_1$-$C_{12}$ alkyl, —C(=O)$NR^{10}R^{11}$, —$NR^{12}$C(=O)$R^{10}$, —$NR^{12}$C(=O)$OR^{11}$, —$NR^{12}$C(=O)$NR^{10}R^{11}$, and $C_1$-$C_{20}$ heteroaryl where $C_1$-$C_{20}$ heteroaryl is optionally substituted with one or more groups independently selected from $C_1$-$C_{12}$ alkyl, $C_1$-$C_{12}$ alkyl-$NR^{10}R^{11}$, $C_1$-$C_{12}$ alkyl-$OR^{10}$, $C_6$-$C_{20}$ aryl, F, Cl, Br, I, —CN, —$CF_3$, —$CO_2$H, —C(=O)$NR^{10}R^{11}$, —$NO_2$, —$NR^{10}R^{11}$, —$NHCOR^{10}$, —$OR^{10}$, —S(O)$_2$$NR^{10}R^{11}$, and —S(O)$_2$$R^{10}$;

$R^2$ is $C_1$-$C_{12}$ alkyl;

$R^3$ is selected from

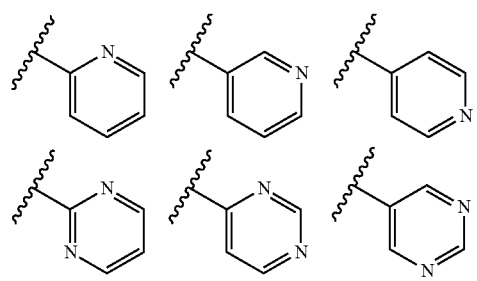

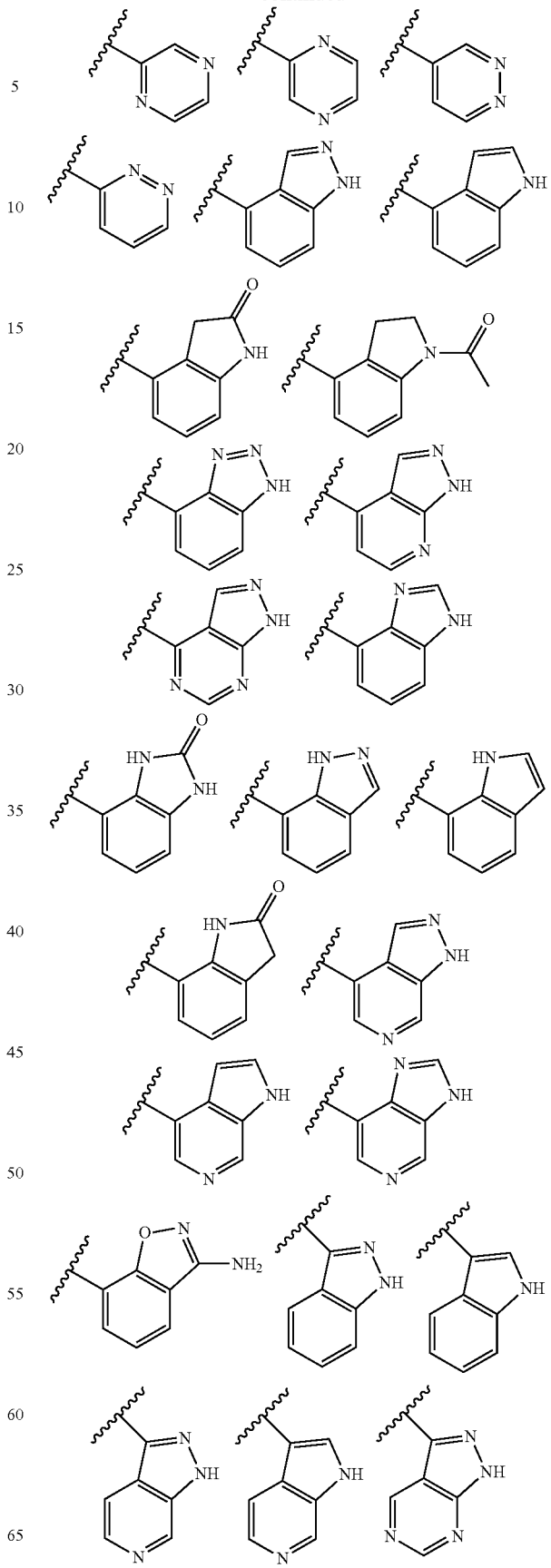

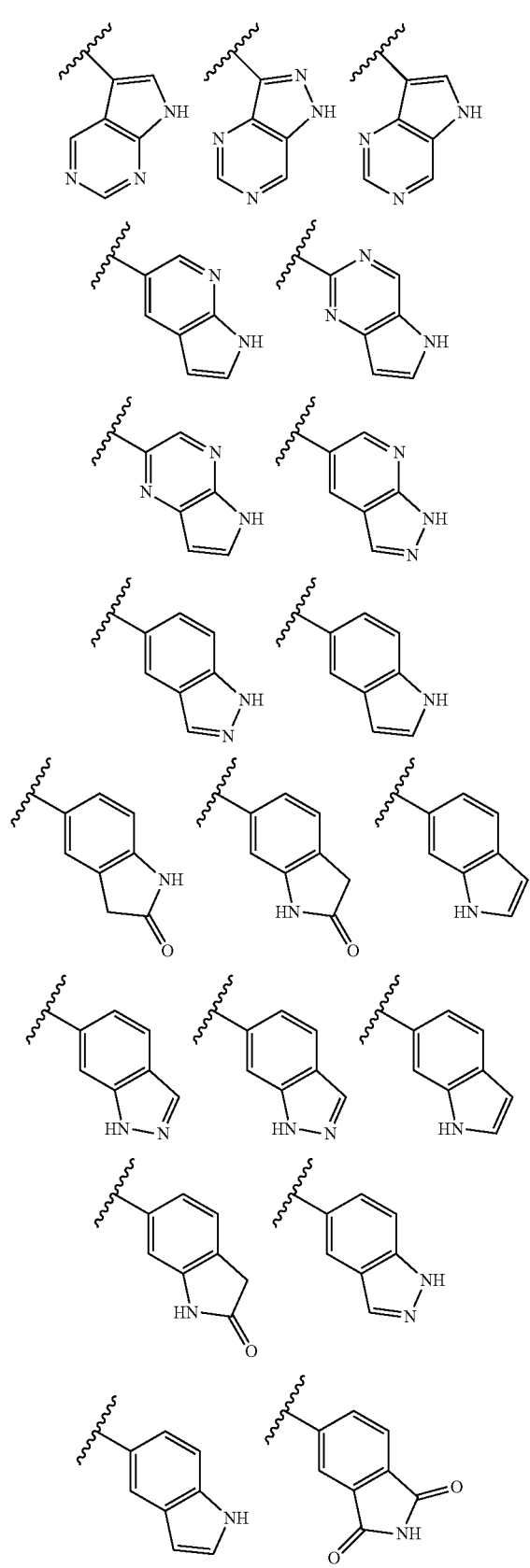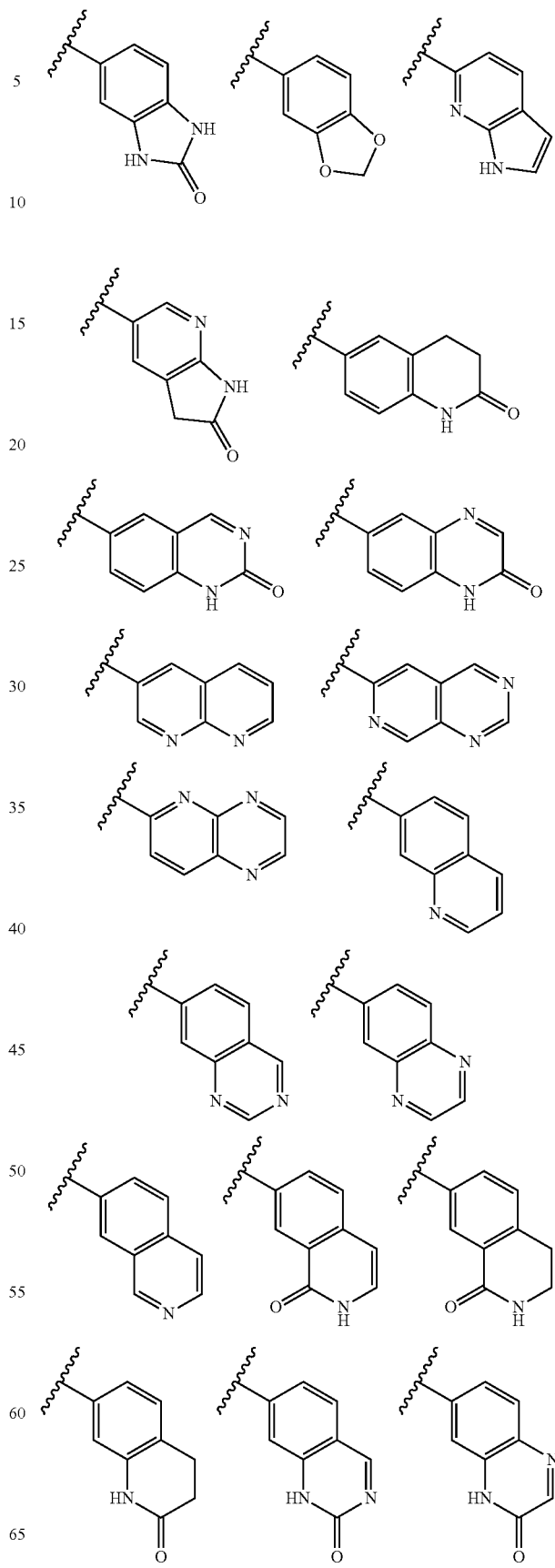

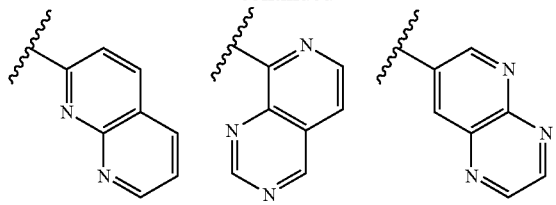

where the wavy line indicates the site of attachment;
optionally substituted with one or more groups independently selected from $C_1$-$C_{12}$ alkyl, $C_6$-$C_{20}$ aryl, F, Cl, Br, I, —$CH_3$, —CN, —$CF_3$, —$CH_2OH$, —$CO_2H$, —$CONH_2$, —$CON(CH_3)_2$, —$NO_2$, —$NH_2$, —$NHCH_3$, —$NHCOCH_3$, —OH, —$OCH_3$, —SH, —NHC($=$O)$NHCH_3$, and —$S(O)_2CH_3$;

$R^4$ is selected from —$NR^{10}R^{13}$, —$NR^{12}C(=O)R^{10}$, —$NR^{10}(C_1$-$C_{12}$ alkyl)$NR^{10}R^{13}$, —$NR^{10}(C_1$-$C_{12}$ alkyl)$OR^{10}$, —$NR^{10}(C_1$-$C_{12}$ alkyl)$C(=O)NR^{10}R^{13}$, —$NR^{10}$($C_1$-$C_{12}$ alkylene)-($C_3$-$C_{12}$ carbocyclyl), —$NR^{10}(C_1$-$C_{12}$ alkylene)-($C_2$-$C_{20}$ heterocyclyl), —$NR^{10}(C_1$-$C_{12}$ alkylene)-($C_6$-$C_{20}$ aryl), —$NR^{10}(C_1$-$C_{12}$ alkylene)-($C_1$-$C_{20}$ heteroaryl), —$OR^{10}$, —O($C_1$-$C_{12}$ alkylene)-($C_3$-$C_{12}$ carbocyclyl), —O($C_1$-$C_{12}$ alkylene)-($C_2$-$C_{20}$ heterocyclyl), —O($C_1$-$C_{12}$ alkylene)-($C_6$-$C_{20}$ aryl), —O($C_1$-$C_{12}$ alkylene)-($C_1$-$C_{20}$ heteroaryl), —($C_1$-$C_{12}$ alkylene)$NR^{10}R^{13}$, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-($C_6$-$C_{20}$ aryl), —($C_1$-$C_{12}$ alkylene)-($C_1$-$C_{20}$ heteroaryl), —($C_2$-$C_8$ alkynylene)$NR^{10}R^{13}$, —($C_2$-$C_8$ alkynylene)-($C_3$-$C_{12}$ carbocyclyl), —($C_2$-$C_8$ alkynylene)-($C_2$-$C_{20}$ heterocyclyl), —($C_2$-$C_8$ alkynylene)-($C_6$-$C_{20}$ aryl), —($C_2$-$C_8$ alkynylene)-($C_1$-$C_{20}$ heteroaryl), —($C_1$-$C_{12}$ alkylene)-($C_6$-$C_{20}$ arylene)-($C_2$-$C_{20}$ heterocyclyl), —($C_6$-$C_{20}$ aryl)-($C_1$-$C_{12}$ alkylene)-($C_2$-$C_{20}$ heterocyclyl), —C($=$O)$NR^{10}R^{11}$, $C_1$-$C_{12}$ alkyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl, where alkyl, alkylene, alkynyl, alkynylene, carbocyclyl, heterocyclyl, aryl, and heteroaryl are optionally substituted with one or more groups independently selected from F, Cl, Br, I, —$CH_3$, —$CH_2OH$, —CN, —$CF_3$, —$CO_2H$, —$COCH_3$, —$CONH_2$, —$CONHCH_3$, —$CON(CH_3)_2$, —$NO_2$, —$NH_2$, —$NHCH_3$, —$NHCOCH_3$, —$NHS(O)_2CH_3$, —OH, —$OCH_3$, —$S(O)_2N(CH_3)_2$, —$SCH_3$, —$CH_2OCH_3$, and —$S(O)_2CH_3$;

$R^{10}$, $R^{11}$ and $R^{12}$ are independently selected from H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl, where alkyl, alkenyl, alkynyl, carbocyclyl, heterocyclyl, aryl, and heteroaryl are optionally substituted with one or more groups independently selected from F, Cl, Br, I, —$CH_2OH$, —$CH_2C_6H_5$, —CN, —$CF_3$, —$CO_2H$, —$CONH_2$, —$CONHCH_3$, —$NO_2$, —$N(CH_3)_2$, —$NHCOCH_3$, —$NHS(O)_2CH_3$, —OH, —$OCH_3$, —$OCH_2CH_3$, —$S(O)_2NH_2$, —$SCH_3$, —$S(O)$$CH_3$, —$CH_2OCH_3$, —$CH_3$, and —$S(O)_2CH_3$;

or $R^{10}$ and $R^{11}$ together with the nitrogen atom to which they are attached form a $C_2$-$C_{20}$ heterocyclyl ring; and $R^{13}$ is selected from $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl, where alkyl, alkenyl, alkynyl, carbocyclyl, heterocyclyl, aryl, and heteroaryl are optionally substituted with one or more groups independently selected from F, Cl, Br, I, —$CH_2OH$, —$CH_2C_6H_5$, —CN, —$CF_3$, —$CO_2H$, —$CONH_2$, —$CONHCH_3$, —$NO_2$, —$N(CH_3)_2$, —$NH$-$COCH_3$, —$NHS(O)_2CH_3$, —OH, —$OCH_3$, —$OCH_2CH_3$, —$S(O)_2NH_2$, —$SCH_3$, —$S(O)CH_3$, —$OCH_2CH_2$—$N(CH_3)_2$, and —$S(O)_2CH_3$;

or $R^{10}$ and $R^{13}$ together with the nitrogen atom to which they are attached form a $C_2$-$C_{20}$ heterocyclyl ring.

2. The compound of claim 1 wherein $R^1$ is H or $CH_3$.

3. The compound of claim 1 wherein $R^2$ is $CH_3$.

4. The compound of claim 1 wherein $R^3$ is a monocyclic heteroaryl selected from:

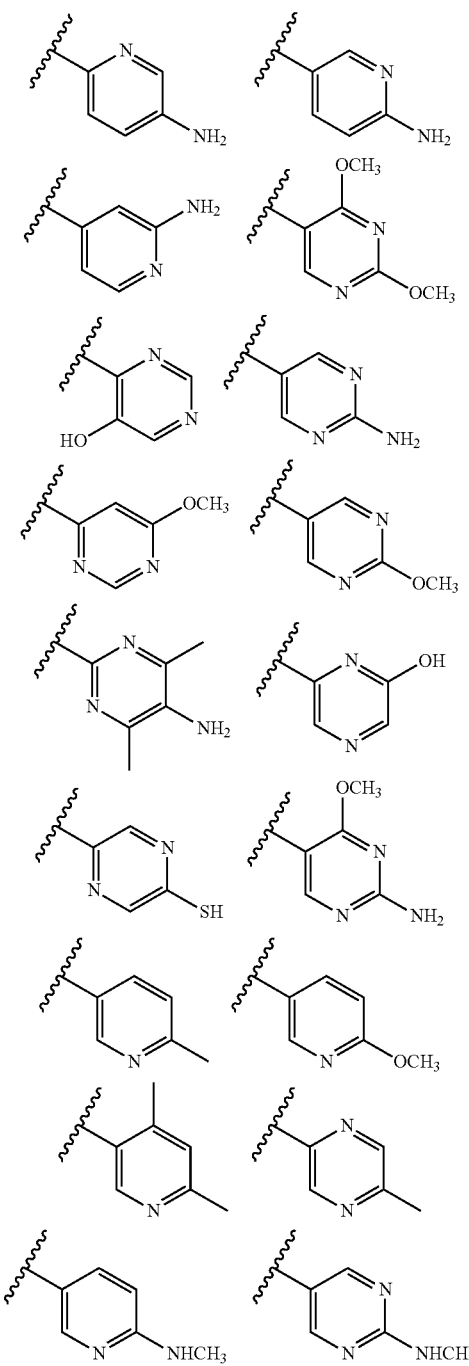

-continued

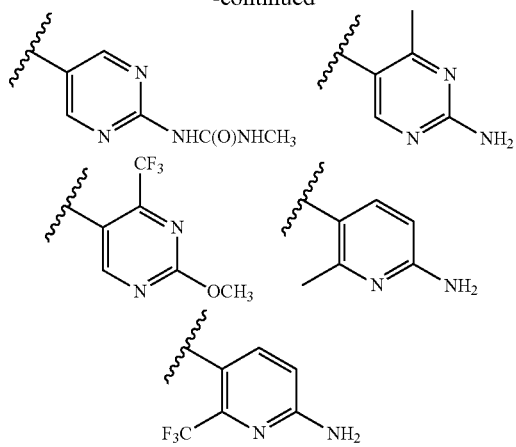

where the wavy line indicates the site of attachment.

5. The compound of claim 1 wherein $R^3$ is selected from:

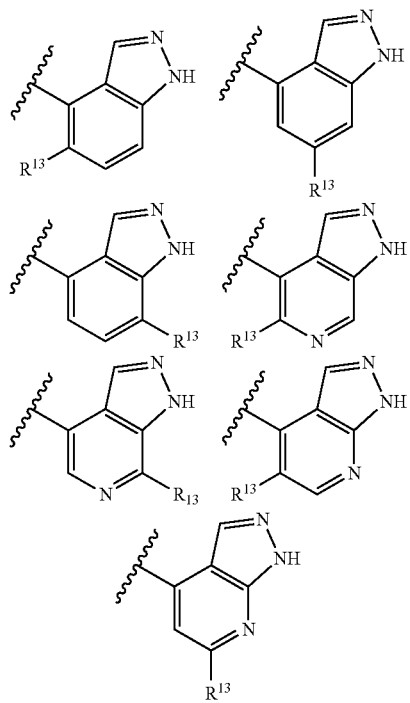

where the wavy line indicates the site of attachment.

6. The compound of claim 1 wherein $R^3$ is 1H-indazol-4-yl.

7. The compound of claim 6 wherein $R^2$ is $CH_3$.

8. The compound of claim 1 wherein $R^3$ is 1H-indol-4-yl.

9. The compound of claim 1 wherein $R^4$ is optionally substituted pyrimidin-5-yl.

10. The compound of claim 1 wherein $R^4$ is optionally substituted $C_6$-$C_{20}$ aryl.

11. The compound of claim 10 wherein $R^4$ is optionally substituted phenyl.

12. The compound of claim 1 wherein $R^4$ is —$OR^{10}$ where $R^{10}$ is optionally substituted phenyl.

13. The compound of claim 12 wherein phenyl is substituted with one or more groups independently selected from —$OCH_3$, —$SO_2CH_3$, —$SO_2NH_2$, —$NHSO_2CH_3$, —$CH_2OCH_3$, —CN, —C(=O)$NH_2$, —C(=O)$NHCH_3$, —NHC(=O)$CH_3$, —$CF_3$, —OH, —$CH_3$, and —Cl.

14. The compound of claim 1 wherein $R^4$ is —$OR^{10}$ where $R^{10}$ is optionally substituted $C_1$-$C_{12}$ alkyl.

15. The compound of claim 1 wherein $R^4$ is —O($C_1$-$C_{12}$ alkylene)-($C_2$-$C_{20}$ heterocyclyl), —O($C_1$-$C_{12}$ alkylene)-($C_6$-$C_{20}$ aryl), or —O($C_1$-$C_{12}$ alkylene)-($C_1$-$C_{20}$ heteroaryl).

16. The compound of claim 1 wherein $R^4$ is —$NR^{10}R^{13}$ where $R^{10}$ is H, $C_1$-$C_{12}$ alkyl, $C_2$-$C_8$ alkenyl, or $C_2$-$C_8$ alkynyl; and $R^{13}$ is optionally substituted phenyl.

17. The compound of claim 1 wherein $R^4$ is —$NR^{10}$($C_1$-$C_{12}$ alkyl)$NR^{10}R^{13}$, —$NR^{10}$($C_1$-$C_{12}$ alkyl)$OR^{10}$, or —$NR^{10}$($C_1$-$C_{12}$ alkyl)C(=O)$NR^{10}R^{13}$.

18. The compound of claim 1 wherein $R^4$ is —$NR^{10}R^{13}$ where $R^{10}$ and $R^{13}$ together with the nitrogen atom to which they are attached form morpholinyl, 4-methylpiperazin-1-yl, 4-methylsulfonylpiperazin-1-yl, or 4-(2-pyridyl)piperazin-1-yl.

19. The compound of claim 1 selected from:
 6-(1H-indazol-4-yl)-1-methyl-4-(4-(methylsulfonyl)phenoxy)-1H-pyrazolo[3,4-b]pyridine;
 6-(1H-indazol-5-yl)-1-methyl-4-(4-(methylsulfonyl)phenoxy)-1H-pyrazolo[3,4-b]pyridine;
 6-(1H-indazol-4-yl)-1-methyl-N-propyl-1H-pyrazolo[3,4-b]pyridin-4-amine;
 6-(1H-indazol-4-yl)-1-methyl-N-(4-(methylsulfonyl)phenyl)-1H-pyrazolo[3,4-b]pyridin-4-amine;
 7-(1-methyl-4-(4-(methylsulfonyl)phenoxy)-1H-pyrazolo[3,4-b]pyridin-6-yl)-1H-indazol-3-amine;
 4-(2,6-dimethylphenoxy)-6-(1H-indazol-4-yl)-1-methyl-1H-pyrazolo[3,4-b]pyridine;
 6-(1H-indazol-4-yl)-4-(3-methoxyphenoxy)-1-methyl-1H-pyrazolo[3,4-b]pyridine;
 4-(3,4-dimethoxyphenoxy)-6-(1H-indazol-4-yl)-1-methyl-1H-pyrazolo[3,4-b]pyridine;
 4-(6-(1H-indazol-4-yl)-1-methyl-1H-pyrazolo[3,4-b]pyridin-4-yloxy)benzamide;
 6-(1H-indazol-4-yl)-1-methyl-4-((1-(methylsulfonyl)piperidin-4-yl)methoxy)-1H-pyrazolo[3,4-b]pyridine;
 3-(6-(H-indazol-4-yl)-1-methyl-1H-pyrazolo[3,4-b]pyridin-4-yl)-N-methylbenzamide;
 N-(3-(6-(1H-indazol-4-yl)-1-methyl-1H-pyrazolo[3,4-b]pyridin-4-yl)phenyl)acetamide;
 N-(3-(6-(1H-indazol-4-yl)-1-methyl-1H-pyrazolo[3,4-b]pyridin-4-yl)phenyl)methanesulfonamide;
 3-(6-(1H-indazol-4-yl)-1-methyl-1H-pyrazolo[3,4-b]pyridin-4-ylamino)-2,2-dimethylpropan-1-ol;
 6-(1H-indazol-4-yl)-1-methyl-4-(4-(methylsulfonyl)phenyl)-1H-pyrazolo[3,4-b]pyridine;
 6-(1H-indazol-4-yl)-1-methyl-N-(3-(methylsulfonyl)propyl)-1H-pyrazolo[3,4-b]pyridin-4-amine;
 6-(6-methoxypyridin-3-yl)-1-methyl-4-(4-(methylsulfonyl)phenoxy)-1H-pyrazolo[3,4-b]pyridine;
 6-(2-methoxypyridin-4-yl)-1-methyl-4-(4-(methylsulfonyl)phenoxy)-1H-pyrazolo[3,4-b]pyridine;
 5-(1-methyl-4-(4-(methylsulfonyl)phenoxy)-1H-pyrazolo[3,4-b]pyridin-6-yl)pyridin-2-ol;
 4-(1-methyl-4-(4-(methylsulfonyl)phenoxy)-1H-pyrazolo[3,4-b]pyridin-6-yl)pyridin-2-ol; and
 7-(1-methyl-4-(4-(methylsulfonyl)phenoxy)-1H-pyrazolo[3,4-b]pyridin-6-yl)benzo[d]isoxazol-3-amine.

20. A pharmaceutical composition comprised of a compound of claim 1 or claim 19 and a pharmaceutically acceptable carrier, glidant, diluent, or excipient.

21. The pharmaceutical composition according to claim 20, further comprising an additional therapeutic agent selected from a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders.

22. A process for making a pharmaceutical composition which comprises combining a compound of claim 1 or claim 19 with a pharmaceutically acceptable carrier.

23. A method of making a Formula I compound comprising reacting a Formula II compound:

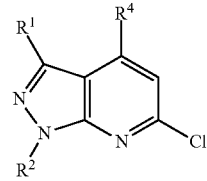

and stereoisomers, geometric isomers, tautomers, or pharmaceutically acceptable salts thereof, with a boronate compound comprising a monocyclic heteroaryl, a fused bicyclic heterocycle, or a fused bicyclic heteroaryl, whereby a Formula I compound is formed:

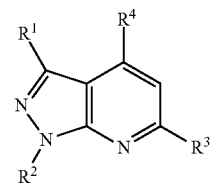

and stereoisomers, geometric isomers, tautomers, or pharmaceutically acceptable salts thereof, wherein:

$R^1$ is selected from H, $C_1$-$C_{12}$ alkyl, —C(=O)NR$^{10}$R$^{11}$, —NR$^{12}$C(=O)R$^{10}$, —NR$^{12}$C(=O)OR$^{11}$, —NR$^{12}$C(=O)NR$^{10}$R$^{11}$, and $C_1$-$C_{20}$ heteroaryl where $C_1$-$C_{20}$ heteroaryl is optionally substituted with one or more groups independently selected from $C_1$-$C_{12}$ alkyl, $C_1$-$C_{12}$ alkyl-NR$^{10}$R$^{11}$, $C_1$-$C_{12}$ alkyl-OR$^{10}$, $C_6$-$C_{20}$ aryl, F, Cl, Br, I, —CN, —CF$_3$, —CO$_2$H, —C(=O)NR$^{10}$R$^{11}$, —NO$_2$, —NR$^{10}$R$^{11}$, —NHCOR$^{10}$, —OR$^{10}$, —S(O)$_2$NR$^{10}$R$^{11}$, and —S(O)$_2$R$^{10}$;

$R^2$ is $C_1$-$C_{12}$ alkyl;

$R^3$ is selected from

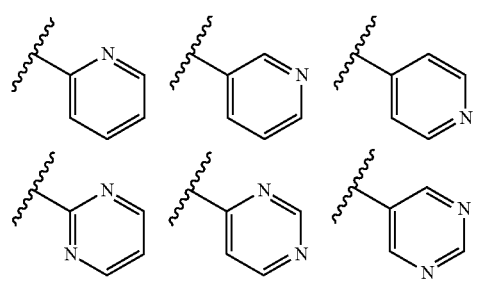

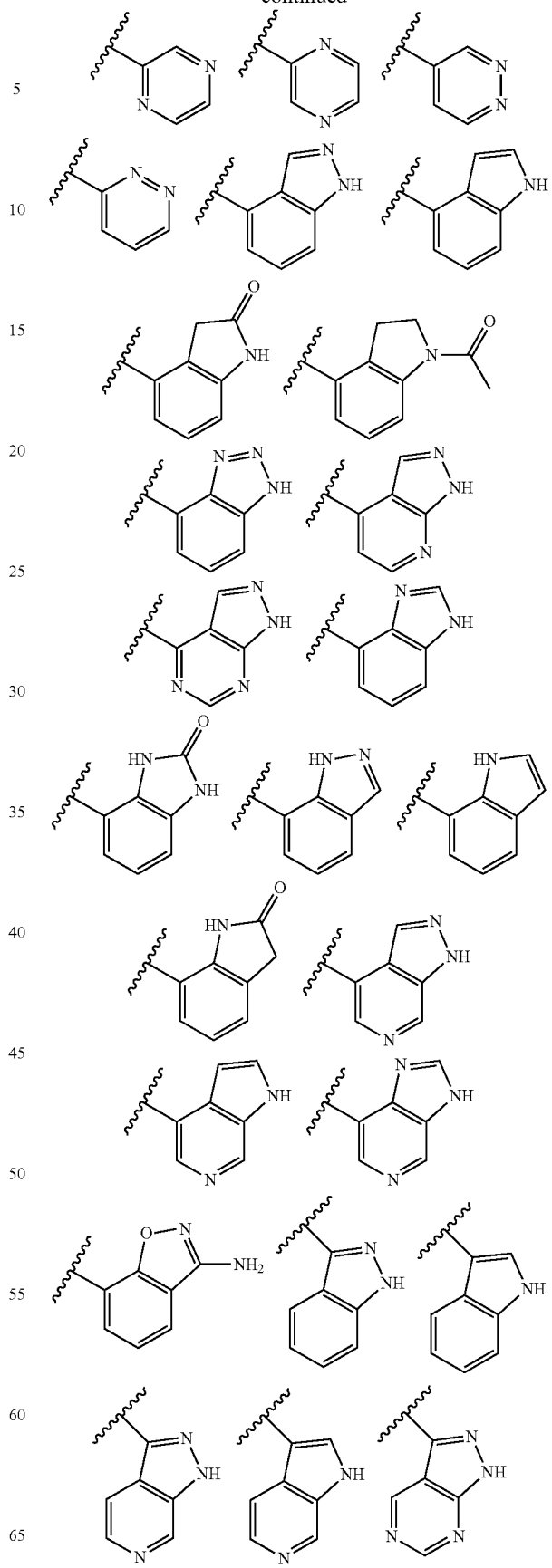

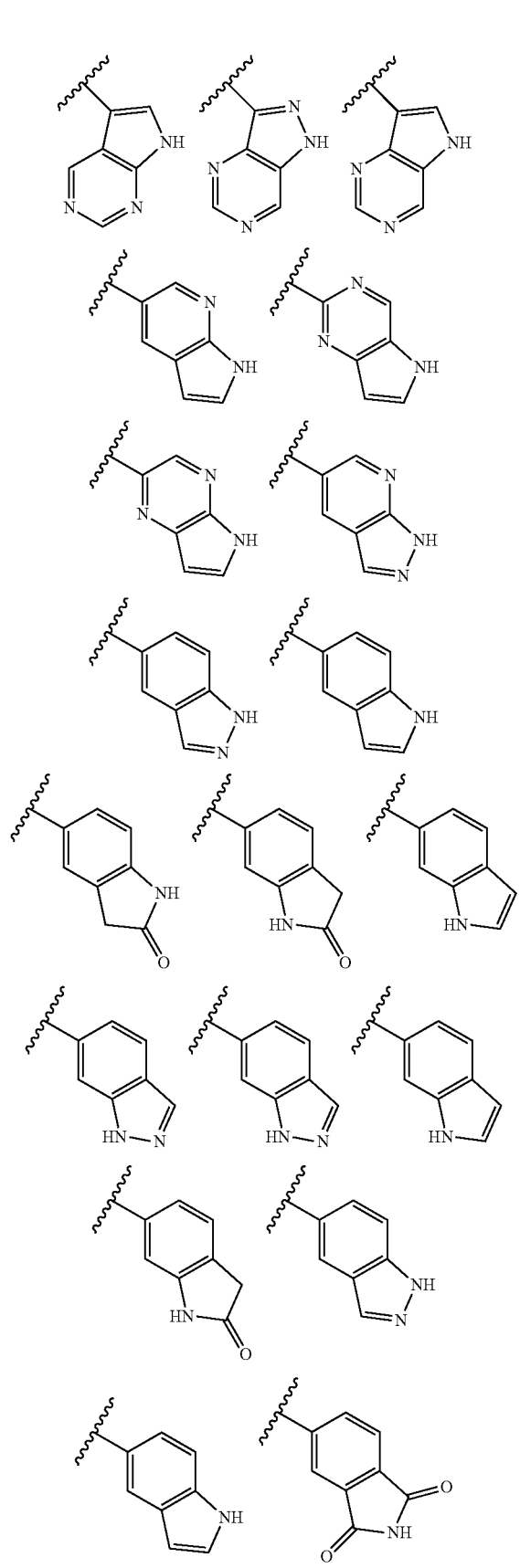
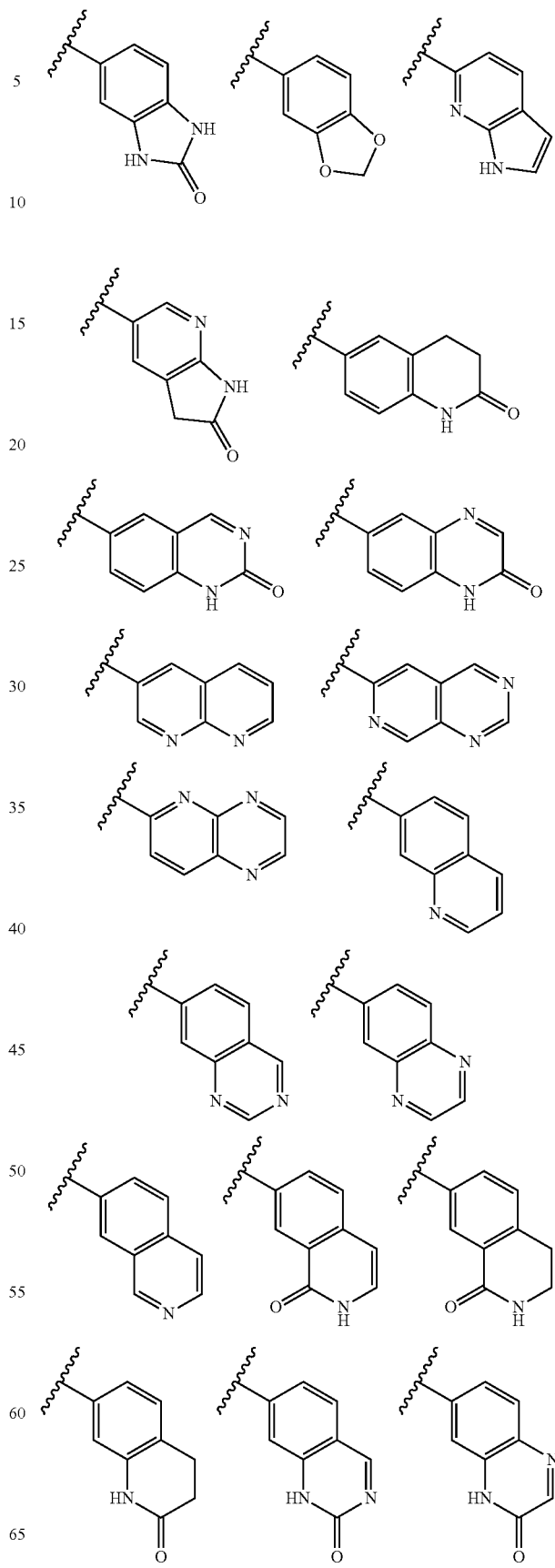

-continued

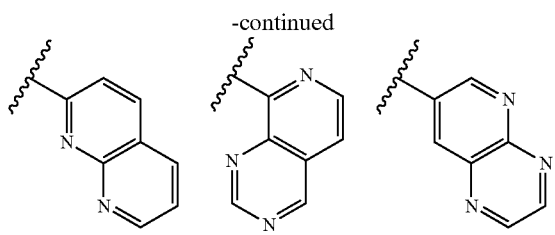

where the wavy line indicates the site of attachment;

optionally substituted with one or more groups independently selected from $C_1$-$C_{12}$ alkyl, $C_6$-$C_{20}$ aryl, F, Cl, Br, I, —$CH_3$, —CN, —$CF_3$, —$CH_2OH$, —$CO_2H$, —$CONH_2$, —$CON(CH_3)_2$, —$NO_2$, —$NH_2$, —$NHCH_3$, —$NHCOCH_3$, —OH, —$OCH_3$, —SH, —NHC(=O)NHCH_3, and —$S(O)_2CH_3$;

$R^4$ is selected from —$NR^{10}R^{13}$, —$NR^{12}C(=O)R^{10}$, —$NR^{10}(C_1$-$C_{12}$ alkyl)$NR^{10}R^{13}$, —$NR^{10}(C_1$-$C_{12}$ alkyl)$OR^{10}$, —$NR^{10}(C_1$-$C_{12}$ alkyl)$C(=O)NR^{10}R^{13}$, —$NR^{10}$($C_1$-$C_{12}$ alkylene)-($C_3$-$C_{12}$ carbocyclyl), —$NR^{10}(C_1$-$C_{12}$ alkylene)-($C_2$-$C_{20}$ heterocyclyl), —$NR^{10}(C_1$-$C_{12}$ alkylene)-($C_6$-$C_{20}$ aryl), —$NR^{10}(C_1$-$C_{12}$ alkylene)-($C_1$-$C_{20}$ heteroaryl), —$OR^{10}$, —$O(C_1$-$C_{12}$ alkylene)-($C_3$-$C_{12}$ carbocyclyl), —$O(C_1$-$C_{12}$ alkylene)-($C_2$-$C_{20}$ heterocyclyl), —$O(C_1$-$C_{12}$ alkylene)-($C_6$-$C_{20}$ aryl), —$O(C_1$-$C_{12}$ alkylene)-($C_1$-$C_{20}$ heteroaryl), —($C_1$-$C_{12}$ alkylene)$NR^{10}R^{13}$, —($C_1$-$C_{12}$ alkylene)-($C_3$-$C_{12}$ carbocyclyl), —($C_1$-$C_{12}$ alkylene)-($C_2$-$C_{20}$ heterocyclyl), —($C_1$-$C_{12}$ alkylene)-($C_6$-$C_{20}$ aryl), —($C_1$-$C_{12}$ alkylene)-($C_1$-$C_{20}$ heteroaryl), —($C_2$-$C_8$ alkynylene)$NR^{10}R^{13}$, —($C_2$-$C_8$ alkynylene)-($C_3$-$C_{12}$ carbocyclyl), —($C_2$-$C_8$ alkynylene)-($C_2$-$C_{20}$ heterocyclyl), —($C_2$-$C_8$ alkynylene)-($C_6$-$C_{20}$ aryl), —($C_2$-$C_8$ alkynylene)-($C_1$-$C_{20}$ heteroaryl), —($C_1$-$C_{12}$ alkylene)-($C_6$-$C_{20}$ arylene)-($C_2$-$C_{20}$ heterocyclyl), —($C_6$-$C_{20}$ aryl)-($C_1$-$C_{12}$ alkylene)-($C_2$-$C_{20}$ heterocyclyl), —$C(=O)NR^{10}R^{11}$, $C_1$-$C_{12}$ alkyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl, where alkyl, alkylene, alkynyl, alkynylene, carbocyclyl, heterocyclyl, aryl, and heteroaryl are optionally substituted with one or more groups independently selected from F, Cl, Br, I, —$CH_3$, —$CH_2OH$, —CN, —$CF_3$, —$CO_2H$, —$COCH_3$, —$CONH_2$, —$CONHCH_3$, —$CON(CH_3)_2$, —$NO_2$, —$NH_2$, —$NHCH_3$, —$NHCOCH_3$, —$NHS(O)_2CH_3$, —OH, —$OCH_3$, —$S(O)_2N(CH_3)_2$, —$SCH_3$, —$CH_2OCH_3$, and —$S(O)_2CH_3$;

$R^{10}$, $R^{11}$ and $R^{12}$ are independently selected from H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl, where alkyl, alkenyl, alkynyl, carbocyclyl, heterocyclyl, aryl, and heteroaryl are optionally substituted with one or more groups independently selected from F, Cl, Br, I, —$CH_2OH$, —$CH_2C_6H_5$, —CN, —$CF_3$, —$CO_2H$, —$CONH_2$, —$CONHCH_3$, —$NO_2$, —$N(CH_3)_2$, —$NHCOCH_3$, —$NHS(O)_2CH_3$, —OH, —$OCH_3$, —$OCH_2CH_3$, —$S(O)_2NH_2$, —$SCH_3$, —$S(O)CH_3$, —$CH_2OCH_3$, —$CH_3$, and —$S(O)_2CH_3$;

or $R^{10}$ and $R^{11}$ together with the nitrogen atom to which they are attached form a $C_2$-$C_{20}$ heterocyclyl ring; and $R^{13}$ is selected from $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl, where alkyl, alkenyl, alkynyl, carbocyclyl, heterocyclyl, aryl, and heteroaryl are optionally substituted with one or more groups independently selected from F, Cl, Br, I, —$CH_2OH$, —$CH_2C_6H_5$, —CN, —$CF_3$, —$CO_2H$, —$CONH_2$, —$CONHCH_3$, —$NO_2$, —$N(CH_3)_2$, —$NHCOCH_3$, —$NHS(O)_2CH_3$, —OH, —$OCH_3$, —$OCH_2CH_3$, —$S(O)_2NH_2$, —$SCH_3$, —$S(O)CH_3$, —$OCH_2CH_2$—$N(CH_3)_2$, and —$S(O)_2CH_3$;

or $R^{10}$ and $R^{13}$ together with the nitrogen atom to which they are attached form a $C_2$-$C_{20}$ heterocyclyl ring.

* * * * *